United States Patent
Morero et al.

(10) Patent No.: US 10,327,791 B2
(45) Date of Patent: Jun. 25, 2019

(54) OCCLUSION BYPASSING APPARATUS WITH A RE-ENTRY NEEDLE AND A DISTAL STABILIZATION BALLOON

(71) Applicant: Medtronic Vascular, Inc., Santa Rosa, CA (US)

(72) Inventors: Massimo Morero, Turin (IT); Giampiero Nicoli, Bergamo (IT); Carlo Guala, Brescia (IT); Giovanni Scalvini, Brescia (IT); Marco Miliani, Brescia (IT); Michele Saputo, Brescia (IT); Claudia Vimercati, Bergamo (IT); Jeffery Argentine, Petaluma, CA (US); Ludwig Compagnoni, Brescia (IT); Davide Zanetti, Brescia (IT); Claudio Silvestro, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 806 days.

(21) Appl. No.: 14/877,351

(22) Filed: Oct. 7, 2015

(65) Prior Publication Data

US 2017/0100141 A1    Apr. 13, 2017

(51) Int. Cl.
*A61M 25/01* (2006.01)
*A61M 25/10* (2013.01)
(Continued)

(52) U.S. Cl.
CPC .......... *A61B 17/22* (2013.01); *A61B 17/3478* (2013.01); *A61M 25/0194* (2013.01);
(Continued)

(58) Field of Classification Search
CPC .......... A61M 25/1027; A61M 25/0194; A61M 25/0084; A61M 25/1002;
(Continued)

(56) References Cited

U.S. PATENT DOCUMENTS

| 3,568,659 A | 3/1971 | Karnegia |
| 4,552,554 A | 11/1985 | Gould et al. |

(Continued)

FOREIGN PATENT DOCUMENTS

| EP | 1765193 | 10/2012 |
| WO | WO2006105244 | 10/2006 |

(Continued)

OTHER PUBLICATIONS

PCT/US2016/055659, The International Search Report and the Written Opinion of the International Searching Authority, dated Jan. 16, 2017.

(Continued)

*Primary Examiner* — Christopher L Templeton
(74) *Attorney, Agent, or Firm* — Medler Ferro Woodhouse & Mills PLLC

(57) ABSTRACT

An occlusion bypassing apparatus for re-entering the true lumen of a vessel after subintimally bypassing an occlusion in a vessel. The apparatus includes an outer shaft component, a needle component, and an inflatable balloon. The outer shaft component has a side port proximal to a distal end thereof and a needle lumen there-through that includes a curved distal portion that terminates at the side port of the outer shaft component. The needle component is configured to be slidably disposed within the needle lumen of the outer shaft component. The inflatable balloon includes a body portion that is disposed distal to the side port of the outer shaft component, and the body portion of the balloon has a flattened profile in an inflated state with first and second chambers that laterally extend from opposing sides of the outer shaft component for stabilizing the apparatus within a subintimal space.

18 Claims, 28 Drawing Sheets

(51) Int. Cl.
*A61B 17/22* (2006.01)
*A61B 17/34* (2006.01)
*A61M 25/00* (2006.01)
*A61M 25/02* (2006.01)
*A61B 17/00* (2006.01)

(52) U.S. Cl.
CPC .............. *A61B 2017/00331* (2013.01); *A61B 2017/22001* (2013.01); *A61B 2017/22069* (2013.01); *A61B 2017/22095* (2013.01); *A61M 25/0084* (2013.01); *A61M 25/1002* (2013.01); *A61M 2025/0092* (2013.01); *A61M 2025/0197* (2013.01); *A61M 2025/0293* (2013.01)

(58) Field of Classification Search
CPC .... A61M 2025/0197; A61M 2025/018; A61M 2025/0087; A61M 2025/009; A61B 2017/22095; A61B 2017/22094
See application file for complete search history.

(56) References Cited

U.S. PATENT DOCUMENTS

| | | | |
|---|---|---|---|
| 4,774,949 A | 10/1988 | Fogarty | |
| 5,002,532 A | 3/1991 | Gaiser et al. | |
| 5,047,045 A * | 9/1991 | Arney | A61M 25/104 604/103.1 |
| 5,217,434 A * | 6/1993 | Arney | A61M 25/0054 604/103.1 |
| 5,250,069 A | 10/1993 | Nobuyoshi et al. | |
| 5,304,134 A * | 4/1994 | Kraus | A61M 25/0045 604/102.02 |
| 5,460,608 A | 10/1995 | Lodin et al. | |
| 5,501,667 A * | 3/1996 | Verduin, Jr. | A61M 25/1002 604/101.01 |
| 5,569,184 A | 10/1996 | Crocker et al. | |
| 5,599,324 A | 2/1997 | McAlister et al. | |
| 5,667,493 A | 9/1997 | Janacek | |
| 5,707,389 A | 1/1998 | Louw et al. | |
| 5,830,222 A | 11/1998 | Makower | |
| 5,916,194 A | 6/1999 | Jacobsen et al. | |
| 5,947,994 A | 9/1999 | Louw et al. | |
| 6,068,638 A | 5/2000 | Makower | |
| 6,071,292 A | 6/2000 | Makower et al. | |
| 6,081,738 A | 6/2000 | Hinohara et al. | |
| 6,159,225 A | 12/2000 | Makower | |
| 6,178,968 B1 | 1/2001 | Louw et al. | |
| 6,190,353 B1 | 2/2001 | Makower et al. | |
| 6,196,230 B1 | 3/2001 | Hall et al. | |
| 6,203,524 B1 | 3/2001 | Burney et al. | |
| 6,210,377 B1 | 4/2001 | Ouchi | |
| 6,217,527 B1 | 4/2001 | Selmon et al. | |
| 6,221,049 B1 | 4/2001 | Selmon et al. | |
| 6,231,546 B1 | 5/2001 | Milo et al. | |
| 6,231,563 B1 | 5/2001 | White et al. | |
| 6,231,587 B1 | 5/2001 | Makower et al. | |
| 6,235,000 B1 | 5/2001 | Milo et al. | |
| 6,261,260 B1 | 7/2001 | Maki et al. | |
| 6,283,983 B1 | 9/2001 | Makower et al. | |
| 6,287,317 B1 | 9/2001 | Makower et al. | |
| 6,302,875 B1 | 10/2001 | Makower et al. | |
| 6,355,027 B1 | 3/2002 | Le et al. | |
| 6,375,615 B1 | 4/2002 | Makower et al. | |
| 6,379,319 B1 | 4/2002 | Garibotto et al. | |
| 6,432,127 B1 | 8/2002 | Kim et al. | |
| 6,447,477 B2 | 9/2002 | Burney et al. | |
| 6,458,098 B1 | 10/2002 | Kanesaka | |
| 6,508,824 B1 | 1/2003 | Flaherty et al. | |
| 6,511,458 B2 | 1/2003 | Milo et al. | |
| 6,514,217 B1 | 2/2003 | Selmon et al. | |
| 6,514,228 B1 | 2/2003 | Hamilton et al. | |
| 6,544,230 B1 | 4/2003 | Flaherty et al. | |
| 6,579,311 B1 | 6/2003 | Makower | |
| 6,602,241 B2 | 8/2003 | Makower et al. | |
| 6,655,386 B1 | 12/2003 | Makower et al. | |
| 6,669,709 B1 | 12/2003 | Cohn et al. | |
| 6,709,444 B1 | 3/2004 | Makower | |
| 6,719,725 B2 | 4/2004 | Milo et al. | |
| 6,726,677 B1 | 4/2004 | Makower et al. | |
| 6,746,464 B1 | 6/2004 | Makower et al. | |
| 7,004,173 B2 | 2/2006 | Sparks et al. | |
| 7,059,330 B1 | 6/2006 | Makower et al. | |
| 7,066,914 B2 | 6/2006 | Andersen | |
| 7,141,041 B2 | 11/2006 | Seward | |
| 7,179,270 B2 | 2/2007 | Makower et al. | |
| 7,316,655 B2 | 1/2008 | Garibotto et al. | |
| 7,357,794 B2 | 4/2008 | Makower et al. | |
| 7,534,223 B2 | 5/2009 | Boutilette et al. | |
| 7,606,615 B2 | 10/2009 | Makower et al. | |
| 7,637,870 B2 | 12/2009 | Flaherty et al. | |
| 7,729,738 B2 | 6/2010 | Flaherty et al. | |
| 7,762,985 B2 * | 7/2010 | Kabrick | A61M 25/104 604/103.07 |
| 7,833,197 B2 | 11/2010 | Boutilette et al. | |
| 7,854,727 B2 | 12/2010 | Belsley | |
| RE42,049 E | 1/2011 | Schroeder et al. | |
| 7,878,986 B2 | 2/2011 | Jen et al. | |
| 7,938,819 B2 | 5/2011 | Kugler et al. | |
| 8,083,727 B2 | 12/2011 | Kugler et al. | |
| 8,172,863 B2 | 5/2012 | Robinson et al. | |
| 8,202,246 B2 | 6/2012 | Kugler et al. | |
| 8,221,357 B2 | 7/2012 | Boutillette | |
| 8,226,566 B2 | 7/2012 | Nita | |
| 8,241,311 B2 | 8/2012 | Ward et al. | |
| 8,257,382 B2 | 9/2012 | Rottenberg et al. | |
| 8,323,261 B2 | 12/2012 | Kugler et al. | |
| 8,337,425 B2 | 12/2012 | Olson et al. | |
| 8,388,876 B2 | 3/2013 | Boutilette et al. | |
| 8,460,254 B2 | 6/2013 | Belsley | |
| 8,486,022 B2 | 7/2013 | Ludwig et al. | |
| 8,496,679 B2 | 7/2013 | Robinson et al. | |
| 8,512,310 B2 | 8/2013 | Kugler et al. | |
| 8,535,245 B2 | 9/2013 | Jen et al. | |
| 8,556,857 B2 | 10/2013 | Boutillette | |
| 9,060,802 B2 | 6/2015 | Kugler | |
| 9,095,374 B2 | 8/2015 | Piccagli | |
| 2001/0000041 A1 | 3/2001 | Selmon et al. | |
| 2002/0072706 A1 | 6/2002 | Hiblar et al. | |
| 2003/0163154 A1 | 8/2003 | Miyata et al. | |
| 2004/0073165 A1 * | 4/2004 | Musbach | A61F 2/958 604/103.07 |
| 2004/0167554 A1 | 8/2004 | Simpson et al. | |
| 2004/0186506 A1 * | 9/2004 | Simpson | A61M 25/0009 606/194 |
| 2005/0021003 A1 | 1/2005 | Caso et al. | |
| 2005/0149062 A1 | 7/2005 | Carroll | |
| 2005/0159728 A1 | 7/2005 | Armour et al. | |
| 2005/0171478 A1 | 8/2005 | Selmon et al. | |
| 2005/0267459 A1 | 12/2005 | Belhe et al. | |
| 2006/0074442 A1 | 4/2006 | Noriega et al. | |
| 2006/0094930 A1 | 5/2006 | Sparks et al. | |
| 2006/0241342 A1 * | 10/2006 | Macaulay | A61B 5/0066 600/104 |
| 2006/0241564 A1 | 10/2006 | Corcoran et al. | |
| 2006/0276749 A1 | 12/2006 | Selmon et al. | |
| 2007/0123925 A1 | 5/2007 | Benjamin et al. | |
| 2008/0125748 A1 | 5/2008 | Patel | |
| 2008/0140101 A1 | 6/2008 | Carley et al. | |
| 2008/0147000 A1 | 6/2008 | Seibel et al. | |
| 2008/0249464 A1 | 10/2008 | Spencer et al. | |
| 2009/0124899 A1 | 5/2009 | Jacobs et al. | |
| 2009/0156998 A1 * | 6/2009 | Arana | A61M 25/0054 604/103 |
| 2009/0192584 A1 | 7/2009 | Gerdts et al. | |
| 2009/0209910 A1 | 8/2009 | Kugler et al. | |
| 2010/0010522 A1 | 1/2010 | Shturman | |
| 2010/0063534 A1 | 3/2010 | Kugler et al. | |
| 2011/0144677 A1 | 6/2011 | Ward et al. | |
| 2011/0264125 A1 | 10/2011 | Wilson et al. | |
| 2011/0276079 A1 | 11/2011 | Kugler et al. | |
| 2012/0053485 A1 | 3/2012 | Bloom | |
| 2012/0095485 A1 | 4/2012 | Cully et al. | |
| 2012/0283571 A1 | 11/2012 | Nita | |

(56) References Cited

U.S. PATENT DOCUMENTS

| | | |
|---|---|---|
| 2012/0283761 A1 | 11/2012 | Rosenthal et al. |
| 2012/0323220 A1 | 12/2012 | Mackay, II et al. |
| 2012/0323251 A1 | 12/2012 | Kugler et al. |
| 2012/0323269 A1 | 12/2012 | Rottenberg et al. |
| 2013/0006167 A1 | 1/2013 | Alvarez |
| 2013/0006173 A1 | 1/2013 | Alvarez et al. |
| 2013/0006282 A1 | 1/2013 | Wilkinson |
| 2013/0072957 A1 | 3/2013 | Anderson |
| 2013/0103070 A1 | 4/2013 | Kugler et al. |
| 2013/0116622 A1 | 5/2013 | Takagi |
| 2013/0150880 A1* | 6/2013 | Anderson .......... A61B 17/3207 606/194 |
| 2013/0158519 A1 | 6/2013 | Boutilette et al. |
| 2013/0245430 A1 | 9/2013 | Selmon et al. |
| 2013/0261545 A1* | 10/2013 | Osypka ............. A61M 25/1002 604/103.02 |
| 2013/0296907 A1 | 11/2013 | Robinson et al. |
| 2013/0304108 A1 | 11/2013 | Weber et al. |
| 2013/0310868 A1 | 11/2013 | Kugler et al. |
| 2013/0317528 A1 | 11/2013 | Anderson et al. |
| 2014/0018732 A1 | 1/2014 | Bagaoisan et al. |
| 2014/0018837 A1 | 1/2014 | Zhou et al. |
| 2014/0142607 A1 | 5/2014 | Cage et al. |
| 2014/0214057 A1 | 7/2014 | Piccagli |
| 2014/0277068 A1 | 9/2014 | Kugler et al. |
| 2015/0032141 A1 | 1/2015 | Silvestro |
| 2015/0032142 A1 | 1/2015 | Silvestro |
| 2015/0112304 A1 | 4/2015 | Silvestro |
| 2015/0174371 A1 | 6/2015 | Schaeffer et al. |
| 2015/0250991 A1 | 9/2015 | Silvestro |

FOREIGN PATENT DOCUMENTS

| | | |
|---|---|---|
| WO | WO2008120209 | 10/2008 |
| WO | WO2009144561 | 12/2009 |
| WO | WO2013003757 | 1/2013 |
| WO | WO2013164825 | 11/2013 |
| WO | WO2014039096 | 3/2014 |

OTHER PUBLICATIONS

Shin et al. "Limitations of the Outback LTD re-entry device in femoropopliteal chronic total occlusions." Journal of Vascular Surgery, vol. 53, 5; 2010.

A. Bolia "Subintimial Angioplasty, the Way Forward" Acta chir belg, 2004, 104, 547-554.

Karkos et al. "Subintimal Recanalization of the Femoropopliteal Segment to Promote Healing of an Ulcerated Below-Knee Amputation Stump" J Endovasc Ther 2006;13:420-423.

Glasby et al. "Subintimal Angioplasty" Review, pp. 12-16, 2008.

Bolia A. "Subintimal Angioplasty, Tips and Technique: How Long Can You Go?".

* cited by examiner

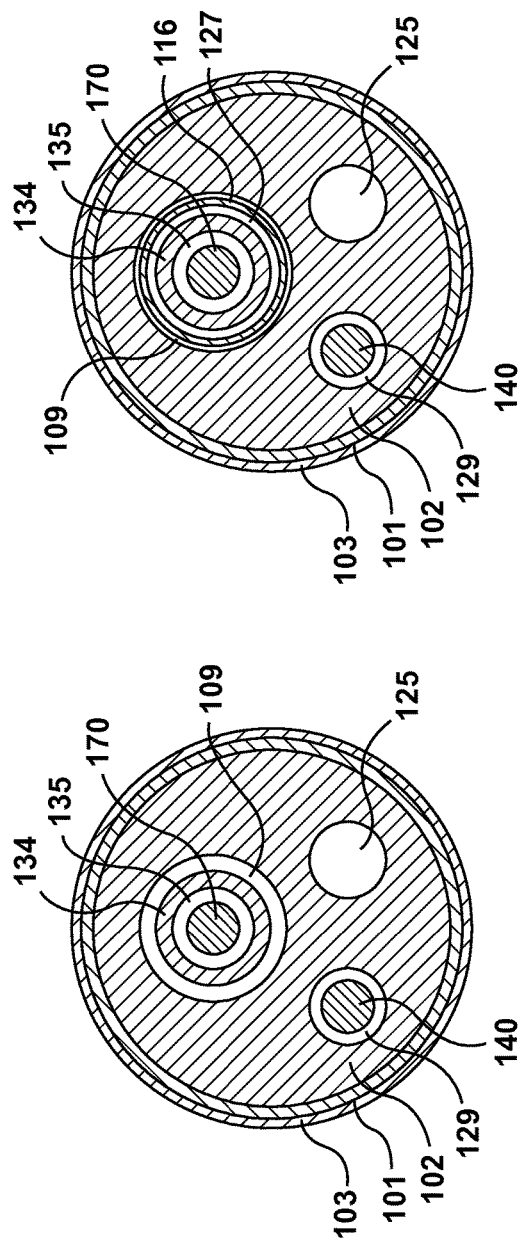
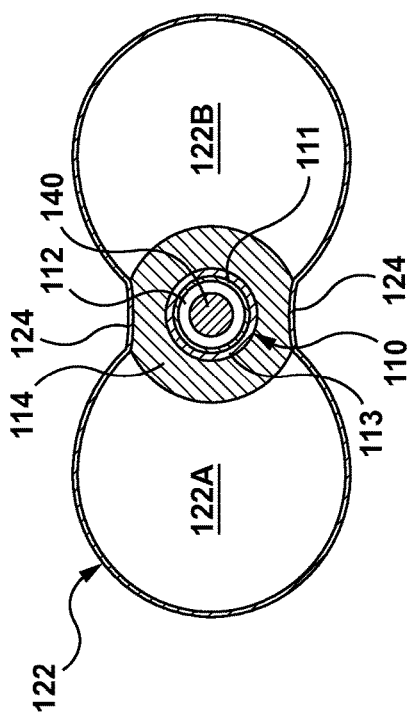
FIG. 1A
FIG. 1B
FIG. 1C

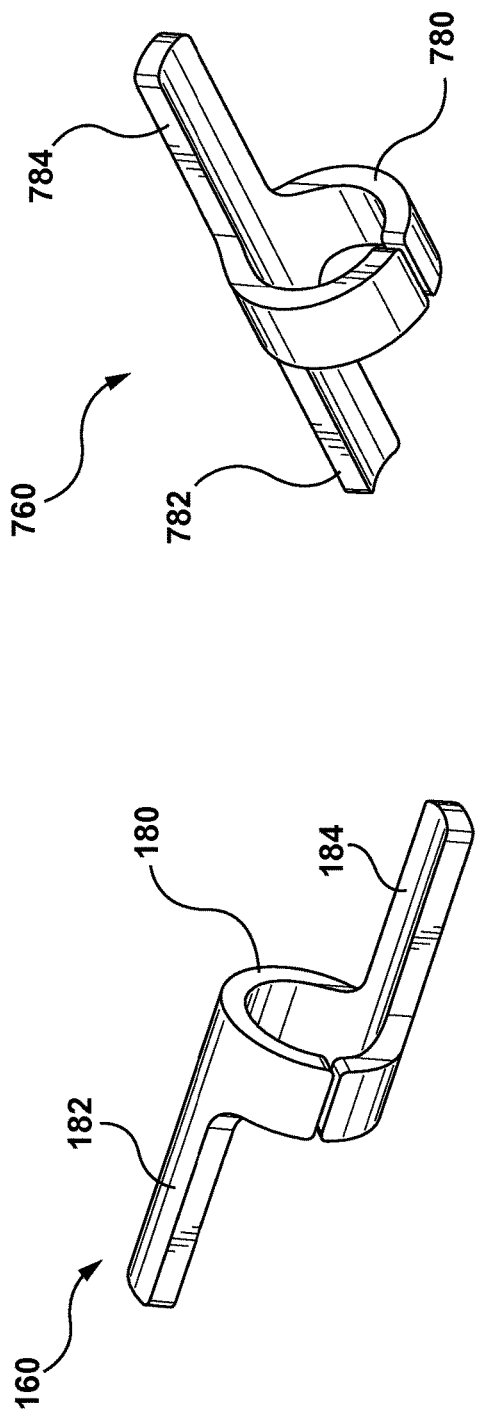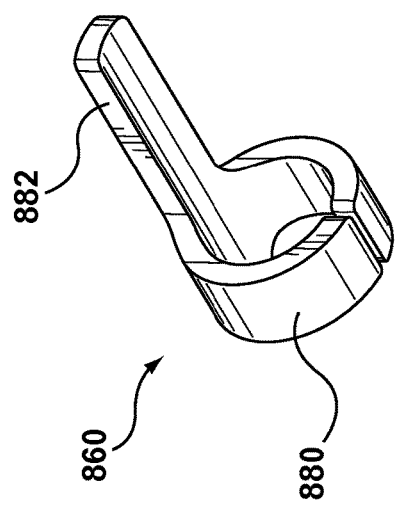

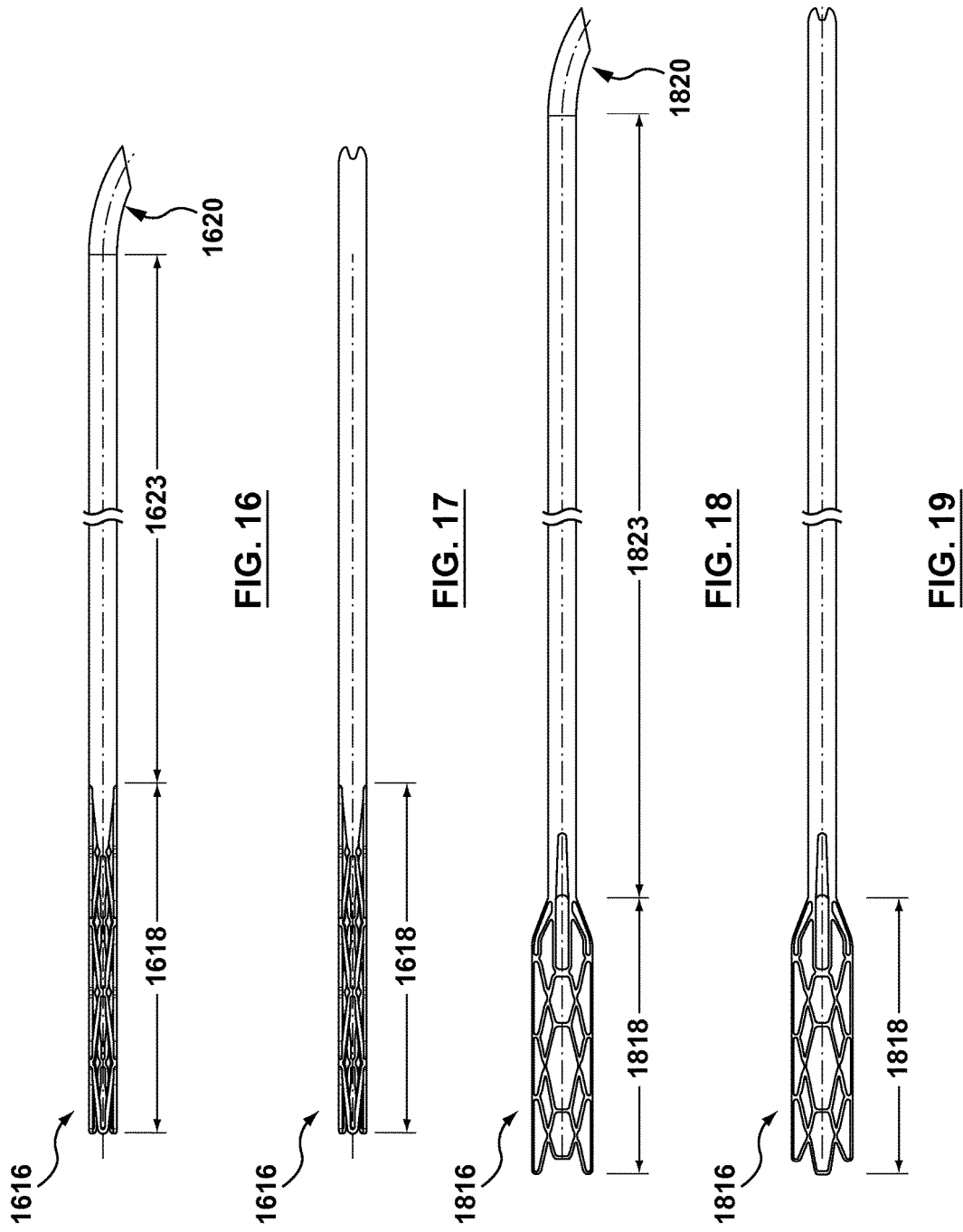

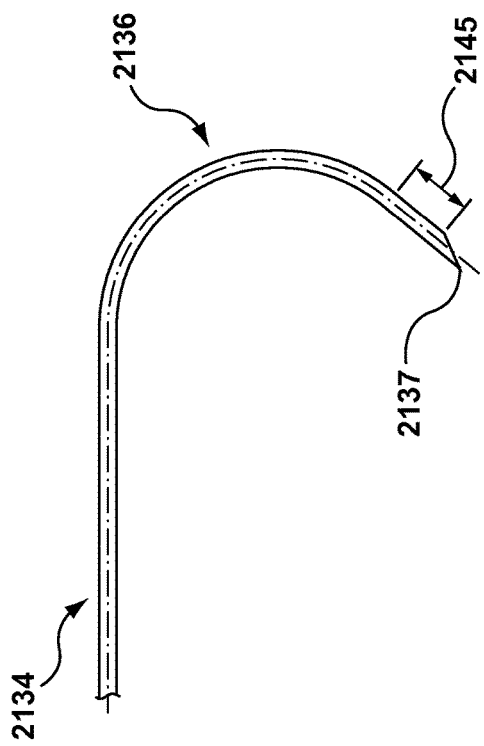
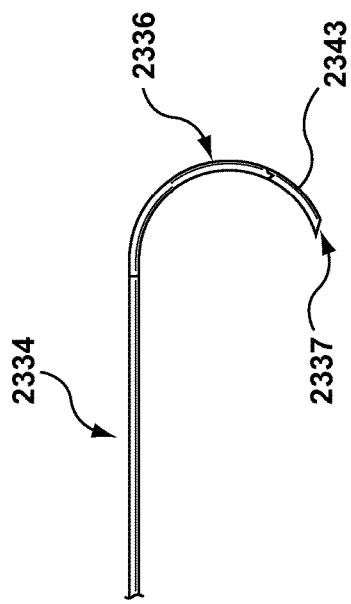
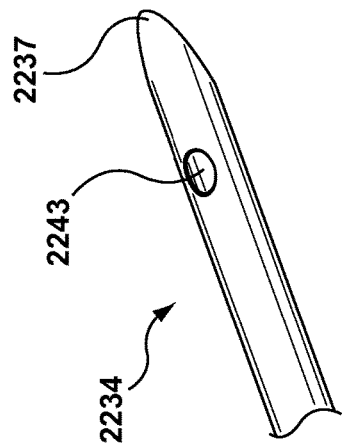
FIG. 21
FIG. 22
FIG. 23

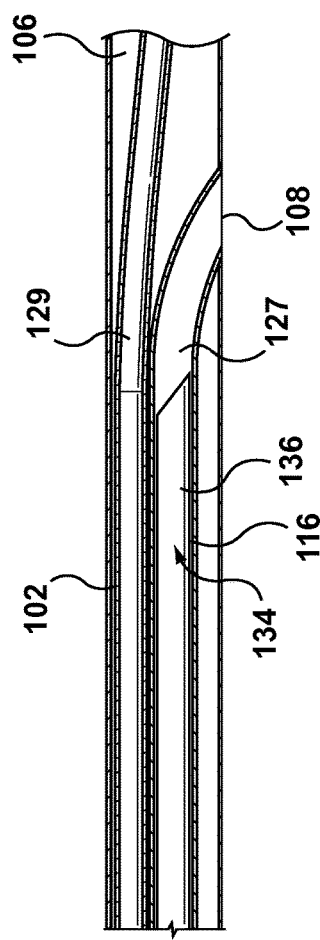
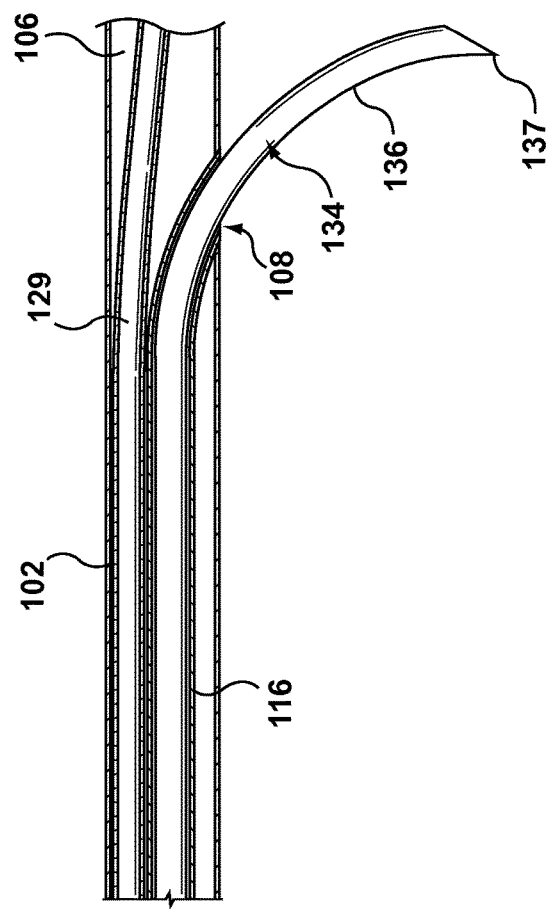
FIG. 24
FIG. 25

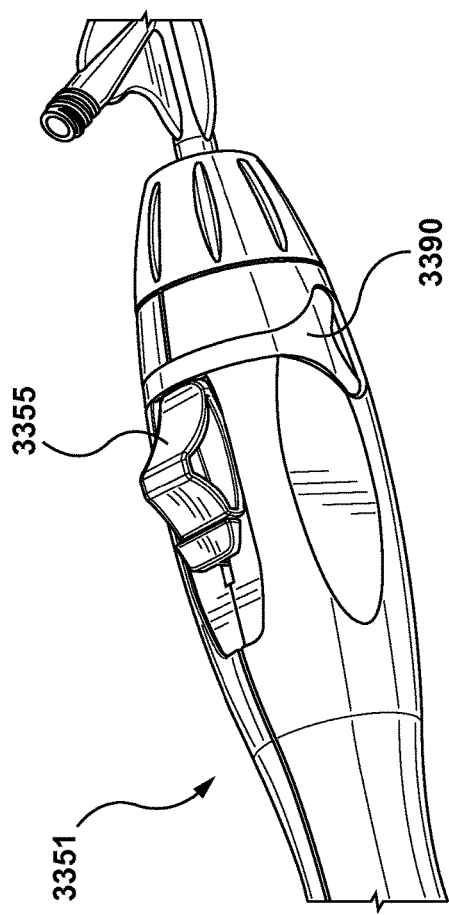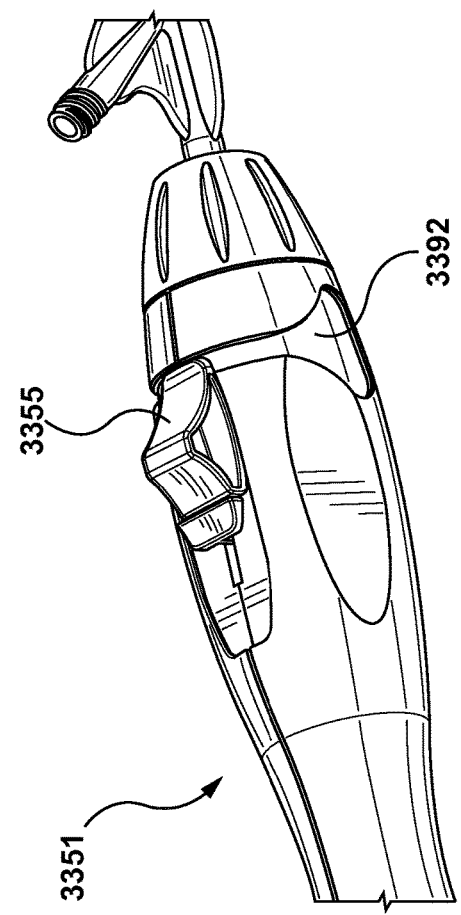
FIG. 33
FIG. 34

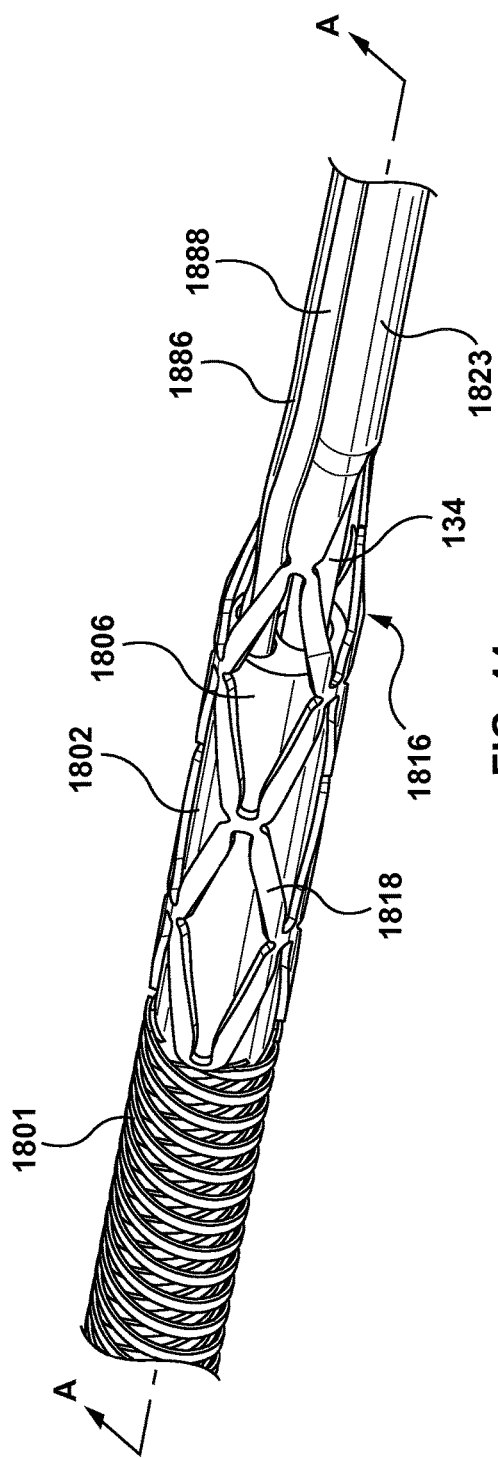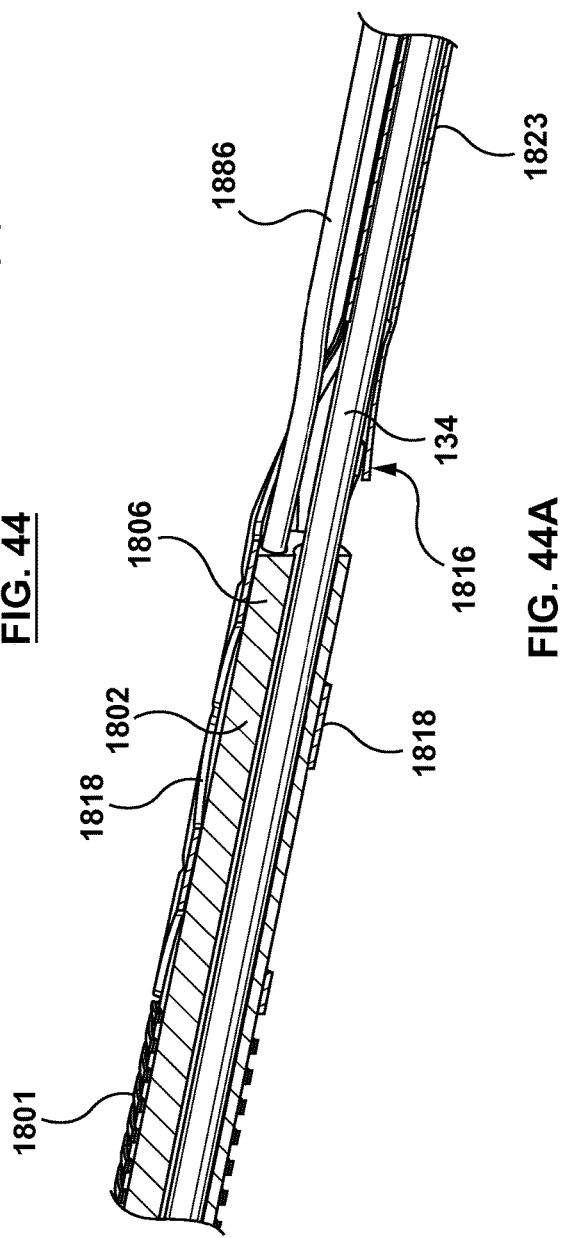
FIG. 44
FIG. 44A

OCCLUSION BYPASSING APPARATUS WITH A RE-ENTRY NEEDLE AND A DISTAL STABILIZATION BALLOON

FIELD OF THE INVENTION

The invention relates generally to an occlusion bypassing apparatus and methods of using the apparatus for subintimally bypassing a blockage in a blood vessel such as a chronic total occlusion and reentering the true lumen of the blood vessel beyond the blockage.

BACKGROUND OF THE INVENTION

Cardiovascular disease, including atherosclerosis, is a serious ailment for many people that may in some cases lead to death. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel.

The anatomy of arteries varies widely from patient to patient. Often a patient's arteries are irregularly shaped, highly tortuous and very narrow. The tortuous configuration of the arteries may present difficulties to a clinician in advancement of the balloon catheter to a treatment site. In addition, in some instances, the extent to which the lumen is narrowed at the treatment site is so severe that the lumen is completely or nearly completely obstructed, which may be described as a total occlusion. Total or near-total occlusions in arteries can prevent all or nearly all of the blood flow through the affected arteries. If the occlusion has been established for a long period of time, the lesion may be referred to as a chronic total occlusion or CTO. Chronic total occlusions can occur in coronary as well as peripheral arteries. Chronic total occlusions are often characterized by extensive plaque formation and typically include a fibrous cap surrounding softer plaque material. This fibrous cap may present a surface that is difficult to penetrate with a conventional medical guidewire.

A number of devices have been developed and/or used for the percutaneous interventional treatment of CTOs, such as stiffer guidewires, low-profile balloons, laser light emitting wires, atherectomy devices, drills, drug eluting stents, and re-entry catheters. The factor that is most determinative of whether the physician can successfully recannalize a CTO is the physician's ability to advance a suitable guidewire from a position within the true lumen of the artery proximal to the CTO lesion, across the CTO lesion, i.e., either through the lesion or around it, and then back into the true lumen of the artery at a location distal to the CTO lesion.

In some cases, such as where the artery is totally occluded by hard, calcified atherosclerotic plaque, the guidewire may tend to deviate to one side and penetrate through the intima of the artery, thereby creating a neo-lumen called a "subintimal tract" i.e., a penetration tract formed within the wall of the artery between the intima and adventitia. In these cases, the distal end of the guidewire may be advanced to a position distal to the lesion but remains trapped within the subintimal tract. In such instances, it is then necessary to divert or steer the guidewire from the subintimal tract back into the true lumen of the artery at a location distal to the CTO lesion. The process of manipulating the guidewire to reenter the artery lumen is often difficult and solutions have been proposed utilizing various means for dealing with such a problem.

A number of catheter-based devices have been heretofore useable to redirect subintimally trapped guidewires back into the true lumen of the artery. Included among these are a variety of catheters having laterally deployable cannulae, i.e., hollow needles. For example, some catheter systems utilize a penetrator or needle that, thanks to the presence of an on-board imaging system (IVUS), exits through a side exit port of the catheter to puncture the intimal layer distal of the CTO to re-enter the true lumen of the vessel. A second guidewire is then passed through the laterally deployed needle and is advanced into the true lumen of the artery. However, a need in the art still exists for other medical catheters or systems that consistently and reliably direct subintimally advanced guidewires back into the true lumen of the artery for the treatment of a CTO.

BRIEF SUMMARY OF THE INVENTION

Embodiments hereof are directed to an apparatus for bypassing an occlusion in a blood vessel. In an embodiment, the apparatus includes an outer shaft component, a needle component, and an inflatable balloon. The outer shaft component has a side port proximal to a distal end thereof. In addition, the outer shaft component includes a needle lumen there-through that includes a curved distal portion that bends from a longitudinal axis of the apparatus and terminates at the side port of the outer shaft component and an inflation lumen there-through configured to receive inflation fluid. The needle component is configured to be slidably disposed within the needle lumen of the outer shaft component and removable therefrom. The inflatable balloon is disposed at the distal end of the outer shaft component and is in fluid communication with the inflation lumen of the outer shaft component. The balloon includes a body portion that is disposed distal to the side port of the outer shaft component, and the body portion of the balloon has a flattened profile in an inflated state with first and second chambers that laterally extend from opposing sides of the outer shaft component for stabilizing the apparatus within a subintimal space.

In another embodiment hereof, the apparatus includes an outer shaft component, a needle component, and an inflatable balloon. The outer shaft component has a side port proximal to a distal end thereof, a needle lumen there-through that includes a curved distal portion that bends from a longitudinal axis of the apparatus and terminates at the side port of the outer shaft component and an inflation lumen there-through configured to receive inflation fluid. The needle component is configured to be slidably disposed within the needle lumen of the outer shaft component and removable therefrom. The inflatable balloon is disposed at the distal end of the outer shaft component and is in fluid communication with the inflation lumen of the outer shaft component. The balloon includes an elongated proximal neck, a body portion, and a distal neck. The elongated proximal neck of the balloon is disposed proximal and distal to the side port of the outer shaft component and the body portion of the balloon is disposed distal to the distal end of the outer shaft component, the body portion of the balloon having a flattened profile in an inflated state with first and second chambers that laterally extend from opposing sides of the outer shaft component for stabilizing the apparatus within a subintimal space. At least one weld extends over the body portion of the balloon to form the first and second chambers thereof.

In another embodiment hereof, the apparatus includes an outer shaft component, a needle housing, a needle component, an inflatable balloon, and a reinforced tubular component. The outer shaft component has a distal port at a distal end thereof and a side port proximal to the distal end thereof. The outer shaft component includes a needle lumen therethrough that includes a curved distal portion that bends from a longitudinal axis of the apparatus and terminates at the side port of the outer shaft component, an inflation lumen therethrough configured to receive inflation fluid, and a guidewire lumen that extends along at least a portion of the outer shaft component and terminates at the distal port of the outer shaft component. The guidewire lumen of the outer shaft component is configured to slidingly receive a guidewire therethrough. The needle housing is disposed within the needle lumen of the outer shaft component, and includes a curved distal portion that defines the curved distal portion of the needle lumen and a transition proximal portion that has a variable flexibility along its length that decreases in a distal direction. The needle component is configured to be slidably disposed within the needle lumen of the outer shaft component and removable therefrom. The inflatable balloon is disposed at the distal end of the outer shaft component and is in fluid communication with the inflation lumen of the outer shaft component. The balloon includes a body portion that is disposed distal to the distal end of the outer shaft component, the body portion of the balloon having a flattened profile in an inflated state with first and second chambers that laterally extend from opposing sides of the outer shaft component for stabilizing the apparatus within a subintimal space. A reinforced tubular component is disposed adjacent to the distal end of the outer shaft component. The reinforced tubular component distally extends beyond the distal end of the outer shaft component through the balloon, and the reinforced tubular component defines a lumen in fluid communication with the guidewire lumen of the outer shaft component.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1A is a cross-sectional view of the occlusion bypassing apparatus of FIG. 1 taken along line A-A thereof, wherein line A-A is located proximal to a needle housing disposed within the occlusion bypassing apparatus.

FIG. 1B is a cross-sectional view of the occlusion bypassing apparatus of FIG. 1 taken along line B-B thereof, wherein line B-B is located through the needle housing.

FIG. 1C is a cross-sectional view of the occlusion bypassing apparatus of FIG. 1 taken along line C-C thereof, wherein line C-C is located through distal to the needle housing and through the expanded lateral balloon of the occlusion bypassing apparatus.

FIG. 6 is a perspective view of a radiopaque marker that may be utilized in embodiments hereof, wherein the radiopaque marker has an S-shape.

FIG. 7 is a perspective view of a radiopaque marker that may be utilized in embodiments hereof, wherein the radiopaque marker has a T-shape.

FIG. 8 is a perspective view of a radiopaque marker that may be utilized in embodiments hereof, wherein the radiopaque marker has an L-shape.

FIG. 16 is a side view of the needle housing of an occlusion bypassing apparatus according to another embodiment hereof, wherein the needle housing is removed from the occlusion bypassing apparatus for illustrative purposes only.

FIG. 17 is a top view of the needle housing of FIG. 16.

FIG. 18 is a side view of the needle housing of an occlusion bypassing apparatus according to another embodiment hereof, wherein the needle housing is removed from the occlusion bypassing apparatus for illustrative purposes only.

FIG. 19 is a top view of the needle housing of FIG. 18.

FIG. 21 is a side view of a distal portion of a needle component according to another embodiment hereof, wherein the needle component includes a straight segment disposed between the curved distal end and the distal tip.

FIG. 22 is a side view of a distal portion of a needle component according to another embodiment hereof, wherein the needle component includes an encapsulated gold marker.

FIG. 23 is a side view of a distal portion of a needle component according to another embodiment hereof, wherein the needle component includes a coated gold distal tip.

FIG. 24 is a partial longitudinal sectional view of the occlusion bypassing apparatus of FIG. 1 taken along a side port thereof, wherein a needle component thereof resides within the needle housing of the occlusion bypassing apparatus.

FIG. 25 is a partial longitudinal sectional view of the occlusion bypassing apparatus of FIG. 1 taken along the side port thereof, wherein a needle component thereof is extended through the side port of an outer shaft component.

FIG. 33 is a side sectional view of a handle that may be utilized in embodiments hereof, wherein the handle includes a stopper and the handle is configured to permit a two-stage needle deployment.

FIG. 34 is a side sectional view of the slider of FIG. 33, wherein the stopper of the handle of FIG. 33 is removed to permit the two-stage needle deployment.

FIG. 44 is a perspective view of a portion of the needle housing of FIGS. 18-19 and the outer shaft component, wherein a polymeric outer or external jacket of the outer shaft component is not shown for clarity purposes only.

FIG. 44A is a sectional view of FIG. 44, taken along line A-A of FIG. 44.

DETAILED DESCRIPTION OF THE INVENTION

Figure 1:
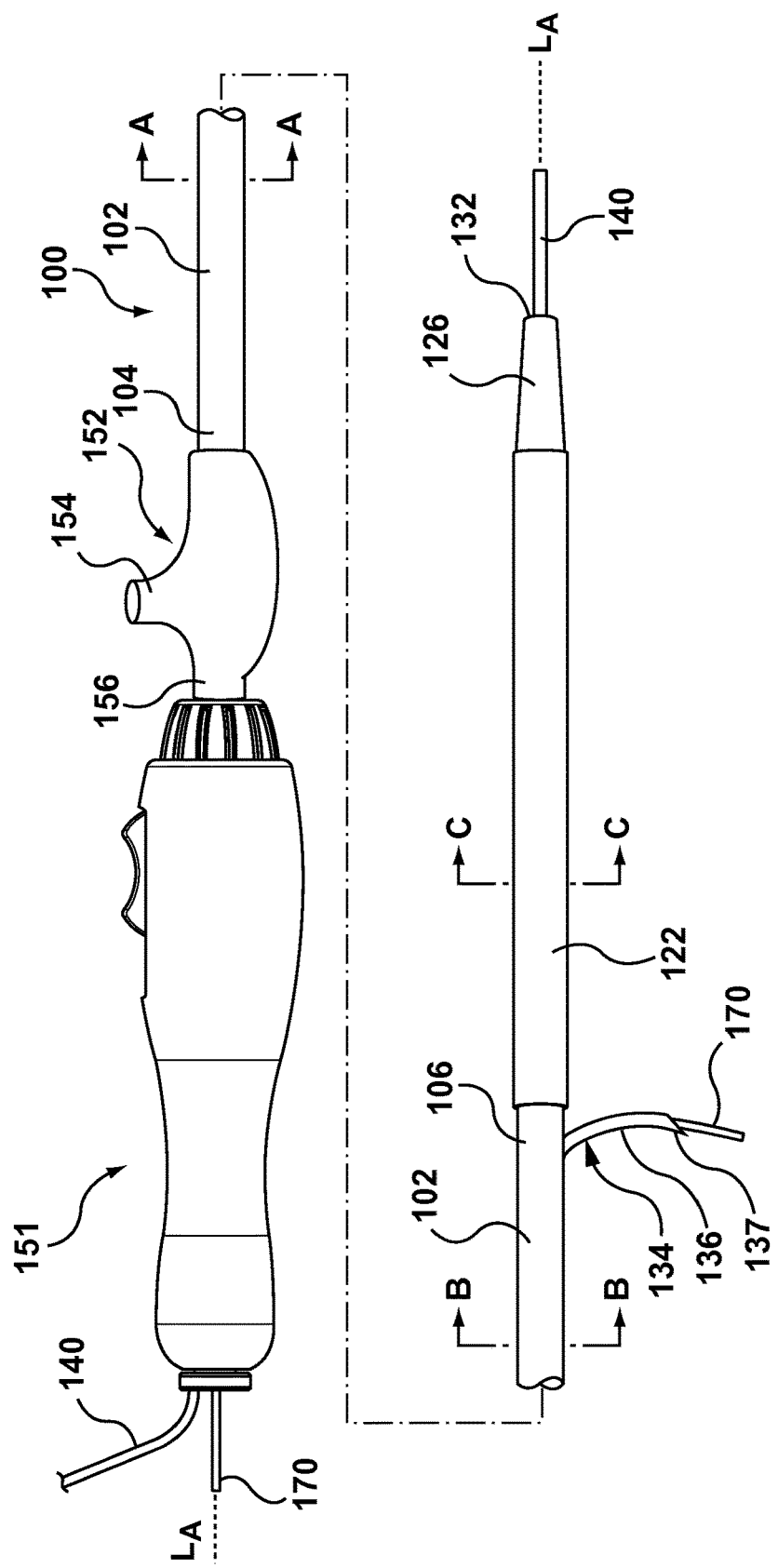
FIG. 1 is a side view of an occlusion bypassing apparatus according to an embodiment hereof, wherein the occlusion bypassing apparatus is shown with two guidewires extending therethrough and the occlusion bypassing apparatus is shown in a deployed configuration in which a needle component thereof is extended through a side port of an outer shaft component and a lateral balloon of the occlusion bypassing apparatus is expanded.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as smaller diameter peripheral or coronary arteries, the invention may also be used in any other body passageways where it is deemed useful. Although the description of the invention generally refers to an apparatus and method of bypassing a vessel blockage in a proximal-to-distal direction, i.e. antegrade or with the blood flow, the invention may be used equally well to bypass a vessel blockage in a distal-to-proximal direction, i.e. retrograde or against the blood flow, if access is available from that direction. In other terms, the apparatus and method described herein may be considered to bypass a vessel blockage from a near side of the blockage to a far side of the blockage. Furthermore, there is no intention to be bound by any expressed or implied theory presented in the preceding technical field, background, brief summary or the following detailed description.

Embodiments hereof relate to an apparatus and method for re-entering the true lumen of a vessel after subintimally bypassing an occlusion in a blood vessel such as a chronic total occlusion (CTO) of an artery. The apparatus includes an outer shaft component having a side port proximal to a distal end thereof, a needle component, and an inflatable balloon. In addition, the outer shaft component includes a needle lumen there-through that includes a curved distal portion that bends from a longitudinal axis of the apparatus and terminates at the side port of the outer shaft component and an inflation lumen there-through configured to receive inflation fluid. The needle component is configured to be slidably disposed within the needle lumen of the outer shaft component and removable therefrom. The inflatable balloon is in fluid communication with the inflation lumen of the outer shaft component and is disposed at a distal end of the outer shaft component, distally extending beyond the distal end of the outer shaft component and thereby forming the distal end of the occlusion bypassing apparatus. More particularly, the balloon includes a body portion that is disposed distal to the distal end of the outer shaft component and the body portion of the balloon has a flattened profile in an inflated state with laterally-extending first and second chambers for stabilizing the apparatus within a subintimal space.

Figure 2:
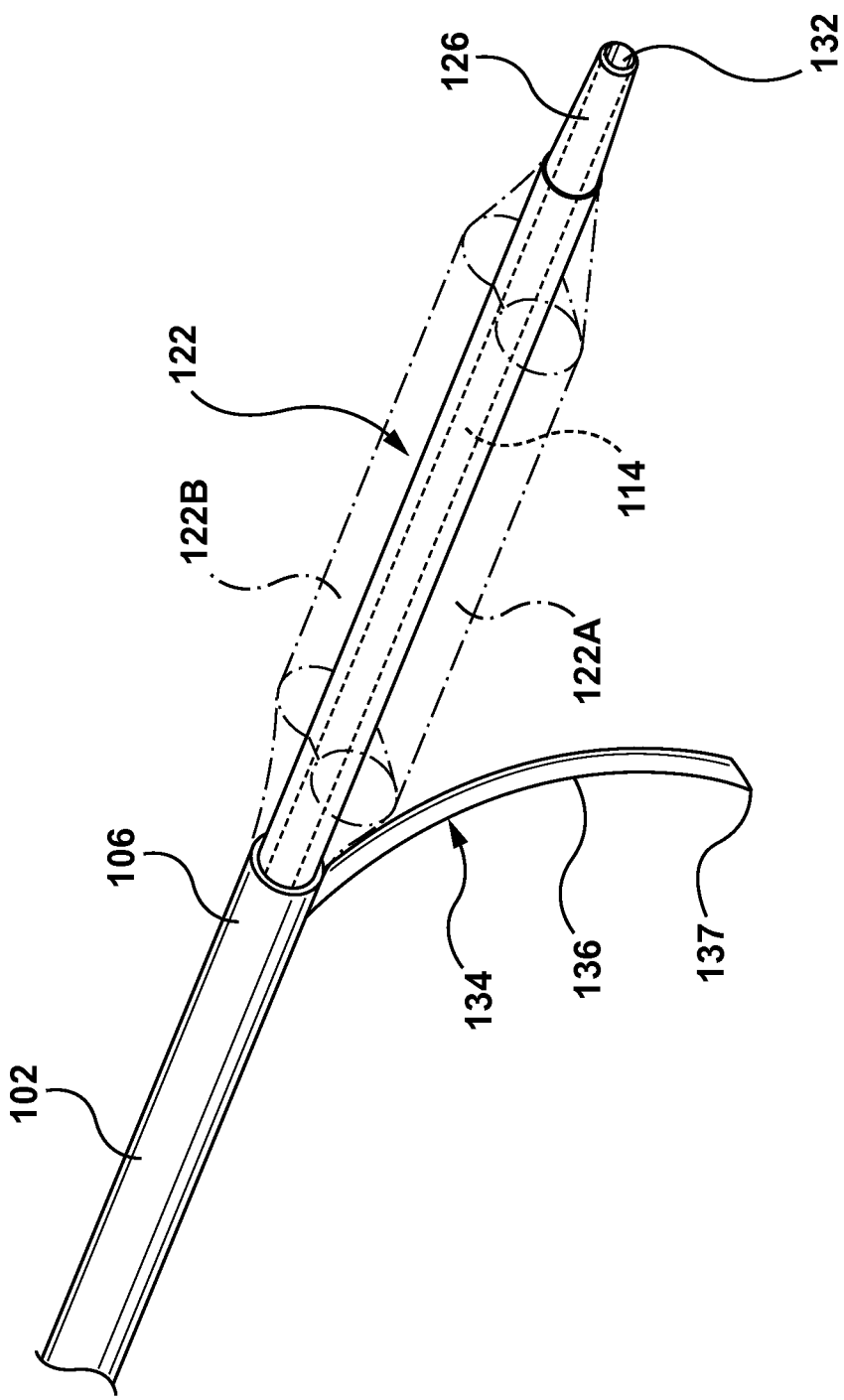
FIG. 2 is a perspective view of a distal portion of the occlusion bypassing apparatus of FIG. 1 with the guidewires removed.
Figure 3:
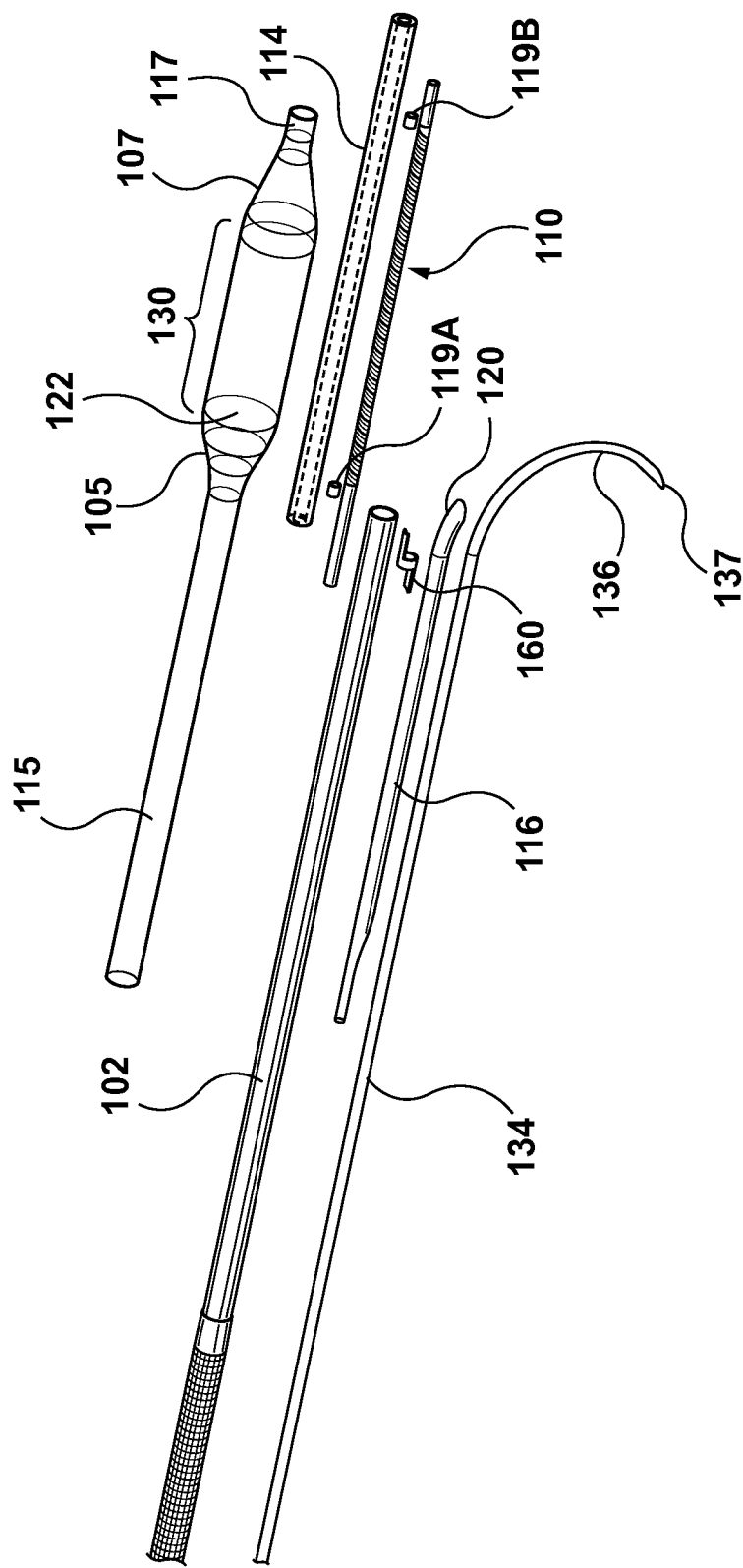
FIG. 3 is an exploded view of FIG. 2.

More particularly, with reference to the figures, FIG. 1 illustrates a side view of an occlusion bypassing apparatus 100 in its deployed configuration, with FIG. 1A, FIG. 1B, FIG. 1C being cross-sectional views which are taken at different longitudinal locations along occlusion bypassing apparatus 100 as described in more detail herein. FIG. 2 is a perspective view of a distal portion of occlusion bypassing apparatus 100 (with the guidewires removed), and FIG. 3 is an exploded view of FIG. 2. Occlusion bypassing apparatus 100 includes an outer shaft component 102 and a balloon 122 for stabilization or anchoring thereof. Outer shaft component 102 will first be described in more detail. Outer shaft component 102 includes a proximal end 104 and a distal end 106. Outer shaft component 102 is a tubular or cylindrical element that defines a plurality of lumens formed by multi-lumen profile extrusion. More particularly, outer shaft component 102 includes a needle lumen 109 for housing a needle component 134, a guidewire lumen 129 for housing a tracking guidewire 140, and an inflation lumen 125 for receiving an inflation fluid.

Proximal end 104 of outer shaft component 102 extends out of the patient and is coupled to a hub 152 of a handle 151. Inflation lumen 125 of outer shaft component 102 is in fluid communication with balloon 122 to allow inflation fluid received through hub 152 to be concurrently delivered to both lateral chambers 122A, 122B (see FIG. 2) of balloon 122, which will be described in more detail herein. As would be understood by one of ordinary skill in the art of balloon catheter design, hub 152 includes a hemostatic valve 156 to accommodate insertion of occlusion bypassing apparatus 100 and a luer 154 or other type of fitting that may be connected to a source of inflation fluid (not shown) and may be of another construction or configuration without departing from the scope of the present invention.

As will be explained in more detail herein, outer shaft component 102 has a side port 108 (see FIGS. 24 and 25) proximal to distal end 106 thereof. Needle lumen 109 includes a curved distal portion that bends from a longitudinal axis of occlusion bypassing apparatus 100 and terminates at side port 108 of outer shaft component 102. A needle component 134 is slidably and removably disposed within needle lumen 109. As used herein, "slidably" denotes back and forth movement in a longitudinal direction. While occlusion bypass apparatus 100 is stabilized or anchored within a subintimal space of a vessel via balloon 122, a curved distal end 136 of needle component 134 is advanced out of side port 108 of outer shaft component 102 towards the true lumen of the vessel. In FIG. 1 and FIG. 2, curved distal end 136 of needle component 134 is shown extended from side port 108 of outer shaft component 102 in a deployed configuration that is suitable for puncturing the vessel wall to gain access to the true lumen. Further, as will be described in more detail herein, needle component 134 is a tubular or cylindrical component that defines a lumen 135 there-through for slidably receiving a reentry guidewire 170. As shown on FIG. 1, when reentry guidewire 170 is introduced into occlusion bypassing apparatus 100, reentry guidewire 170 extends proximally from handle 151 and extends distally from a distal tip 137 of needle component 134.

Guidewire lumen 129 of outer shaft component 102 extends the entire length thereof for accommodating tracking guidewire 140 in a so-called over-the-wire configuration. As will be described in more detail herein, occlusion bypassing apparatus 100 includes a guidewire reinforcement component 110 (see FIG. 1C). Guidewire reinforcement component 110 defines a lumen 112 that is in fluid communication with guidewire lumen 129 of outer shaft component. Guidewire reinforcement component 110 distally extends from or beyond distal end 106 of outer shaft component 102. In an embodiment hereof, a proximal end of guidewire reinforcement component 110 may be disposed adjacent to distal end 106 of outer shaft component 102 and may or may be in direct contact with distal end 106 of outer shaft component 102. As will be described in more detail herein, a build-up tube 114 is disposed over or surrounds guidewire reinforcement component 110. A flexible distal tip 126 is bonded or otherwise coupled to a distal end of build-up tube 114. Flexible distal tip 126 forms a distal guidewire port 132, as best shown on FIG. 2. Thus, the guidewire lumen for occlusion bypassing apparatus 100 is collectively formed via guidewire lumen 129 of outer shaft component 102, lumen 112 of guidewire reinforcement component 110, and distal tip 126 that forms distal guidewire port 132. The guidewire lumen for occlusion bypassing apparatus 100 is sized to slidingly receive tracking guidewire 140 so that occlusion bypassing apparatus 100 may be tracked thereover. As shown on FIG. 1, when occlusion bypassing apparatus 100 is tracked over tracking guidewire 140, tracking guidewire 140 extends proximally from handle 151 and extends distally from distal tip 126. Tracking guidewire 140 is omitted from FIG. 2 and FIG. 3 in order to clearly show distal guidewire port 132. In an embodiment, outer shaft component 102 may be sized to be used with a 5F introducer sheath with lumen 112 of guidewire reinforcement component 110 being sized to accommodate a guidewire having an outer diameter of 0.014 inch.

As shown on the cross-sectional FIG. 1A and FIG. 1B, in an embodiment hereof, outer shaft component 102 is formed as a composite having a reinforcement layer incorporated within a polymeric body in order to enhance strength and/or flexibility and/or torquability. More particularly, outer shaft component 102 may include a braided or reinforcement layer 101 disposed thereover and a polymeric outer or external jacket 103 disposed over reinforcement layer 101. More particularly, outer shaft component 102 may be formed of one or more polymeric materials, non-exhaustive examples of which include polyethylene, polyethylene block amide copolymer (PEBA), polyurethane (PU), polyamide and/or combinations thereof, either laminated, blended or co-extruded. Outer shaft component 102 may have a polymer hardness varying in the range of 55 to more than 70 Shore A units, including the variation of the nature of polymer. Suitable reinforcement layers for reinforcement layer 101 include braiding, wire mesh layers, embedded axial wires, embedded helical or coiled wires, hypotubes, and the like. In an embodiment, reinforcement layer 101 surrounds outer shaft component 102 and is a stainless steel braid reinforcement having a PPI (picks per inch of length) ranging between 30 to 80. In an embodiment, the stiffness or flexibility of reinforcement layer 101 varies along its length such that a continuous variation of PPI results in a gradual variation of stiffness of outer shaft component 102. Reinforcement layer 101 may include a stainless steel flat or ribbon wire having the thickness varying in the range 0.0005 to 0.005 inches and a width in the range of 0.001 to 0.01 inches. In another embodiment, reinforcement layer 101 may include a round wire with diameter varying in the range of 0.001 to 0.005 inches. Further, the number of wires used for reinforcement layer 101 may vary and in one embodiment may range between 8 and 16. Outer or external jacket 103, which is disposed over or surrounds reinforcement layer 101, holds down reinforcement layer 101 and provides a smooth outermost. Outer jacket 103 may be formed of one or more polymeric materials, non-exhaustive examples of which include polyethylene, polyethylene block amide copolymer (PEBA), polyurethane (PU), polyamide and/or combinations thereof, either laminated, blended or co-extruded. Although described herein as extending the full length of outer shaft component 102, outer jacket 103 and reinforcement layer 101 may extend only over a portion of outer shaft component. In one embodiment, for example, at least a proximal portion of outer shaft component 102 may include outer jacket 103 and reinforcement layer 101.

Other types of construction are suitable for outer shaft component 102. In another embodiment (not shown), rather than a single inflation lumen that concurrently delivers inflation fluid to both first and second lateral chambers 122A, 122B of balloon 122 as described herein, the outer shaft component may include two inflation lumens that separately deliver inflation fluid to the first and second lateral chambers. Further, although embodiments of outer shaft component 102 are described above with a relatively long guidewire lumen in an over-the-wire configuration, embodiments hereof may be modified to have a rapid-exchange configuration in which the guidewire lumen extends only along a distal portion of the outer shaft component. For example, in order to provide a rapid-exchange configuration, the relatively long guidewire lumen of the above embodiment may be modified to extend only along a distal portion of the outer shaft component and may have a length between 5 cm and 20 cm.

Balloon 122 will now be described in more detail. As best shown on the cross-sectional view of FIG. 1C taken along line C-C of FIG. 1 and the perspective view of FIG. 2, balloon 122 is formed such that upon inflation balloon 122 includes two lateral chambers 122A, 122B are disposed in parallel on opposing sides of occlusion bypassing apparatus 100. Lateral chambers 122A, 122B have a flattened or laterally-extending profile when in an inflated state to anchor occlusion bypassing apparatus 100 within the anatomy, more particularly within the subintimal space of the vessel wall when utilized in the treatment of a CTO, so as to provide stability to occlusion bypassing apparatus 100. Side port 108 of outer shaft component 102, through which needle component 134 is advanced, is proximal to lateral chambers 122A, 122B of balloon 122. Accordingly, lateral chambers 122A, 122B of balloon 122 are distal to the reentry point of needle component 134 in vivo. When inflated, balloon 122 acts as stabilization for needle component 134 and when deflated, balloon 122 is sufficiently flexible to permit maneuvering of the distal end of occlusion bypassing apparatus 100. When inflated, balloon 122 varies the overall stiffness of the distal end of occlusion bypassing apparatus 100, contributing to stabilize the apparatus during the deployment of needle component 134 in its most active stage. Balloon 122 further contributes to prevent axial dislodgement of occlusion bypassing apparatus 100, as well as to orient of occlusion bypassing apparatus 100 towards the vessel true lumen during inflation thereof.

More particularly, as previously described, guidewire reinforcement component 110 distally extends beyond distal end 106 of outer shaft component 102. With reference to FIG. 1C and FIG. 3, guidewire reinforcement component 110 is a tubular or cylindrical composite element that defines lumen 112 there-through and includes a reinforcement layer 111 and a polymeric body or jacket 113 disposed over reinforcement layer 111. Suitable reinforcement layers for layer 111 include braiding via a ribbon or round wire, wire mesh layers, embedded axial wires, embedded helical or coiled wires, hypotubes, and the like. Outer jacket 113 may be formed of one or more polymeric materials, non-exhaustive examples of which include polyethylene, polyethylene block amide copolymer (PEBA), polyurethane (PU), polyamide and/or combinations thereof, either laminated, blended or co-extruded. In an embodiment, reinforcement layer 111 is helical or coiled to prevent kinking and outer jacket 113 is a PI/PTFE composite tube to provide lubricity.

As best shown on the exploded view of FIG. 3 and stated above, occlusion bypassing apparatus 100 also includes build-up tube 114 disposed over or surrounding guidewire reinforcement component 110. Build-up tube 114 is a tubular or cylindrical element that may be formed of one or more polymeric materials, non-exhaustive examples of which include polyethylene, polyethylene block amide copolymer (PEBA), polyurethane (PU), polyamide and/or combinations thereof, either laminated, blended or co-extruded. Build-up tube 114 functions to embed or cover guidewire reinforcement component 110, and also provides a substrate for bonding or otherwise attaching balloon 122. Build-up tube 114 ends in within distal tip 126, which is bonded thereto.

As best shown on FIG. 3, balloon 122 includes a body portion 130, an elongated proximal neck 115, a distal neck 117, a proximal cone 105, and a distal cone 107. In an embodiment hereof, body portion 130 has a length that ranges between 9 mm and 13 mm, distal neck 117 has a length that ranges between 5 mm and 7 mm, and elongated proximal neck length has a length that ranges between 30 mm to 36 mm. When balloon 122 is inflated, body portion 130 of balloon 122 forms or includes lateral chambers 122A, 122B of balloon 122 as will be described in more detail herein with respect to FIGS. 4-5. Proximal cone 105 extends between elongated proximal neck 115 and body portion 130 of balloon 122, while distal cone 107 extends between distal neck 117 and body portion 130 of balloon 122 such that body portion 130 of balloon 122 extends between or is sandwiched elongated proximal neck 115 and a distal neck 117. When balloon 122 is inflated, each of proximal and distal cones 105, 107, respectively, extends between a 30 and 40 degree angle relative to the longitudinal axis of occlusion bypassing apparatus 100. In an embodiment, distal cone 107 extends at a 30 degree angle relative to the longitudinal axis of occlusion bypassing apparatus 100 and proximal cone 105 extends at a 40 degree angle relative to the longitudinal axis of occlusion bypassing apparatus 100. The relative angles of the proximal and distal cones may be differentiated to accomplish distally, a smoother transition to distal tip 126 using a 30 degrees distal cone 107, and proximally to minimize the distance in between outer shaft component 102 and body portion 130 of balloon 122 with 40 or more degrees.

When assembled into occlusion bypassing apparatus 100, elongated proximal neck 117 of balloon 122 is disposed over and bonded to outer shaft component 102 such that elongated proximal neck 117 is disposed or spans over both proximal and distal to side port 108 of the outer shaft component. Body portion 130 (and lateral chambers 122A, 122B thereof) are disposed distal to distal end 106 of outer shaft component and may be considered as forming the distal end of occlusion bypassing apparatus 100. Distal neck 117 of balloon 122 is disposed over and bonded to build-up tube 114. As best shown on FIG. 1C, build-up tube 114 and guidewire reinforcement component 110 disposed therethrough extend through body portion 130 of balloon 122, with lateral chambers 122A, 122B disposed in parallel on opposing sides of build-up tube 114 upon inflation of balloon 122. Body portion 130 of balloon 122 thus has a flattened profile in an inflated state due to lateral chambers 122A, 122B that laterally extend from opposing sides of build-up tube 114 for stabilizing occlusion bypassing apparatus 100 within a subintimal space.

Figure 4:
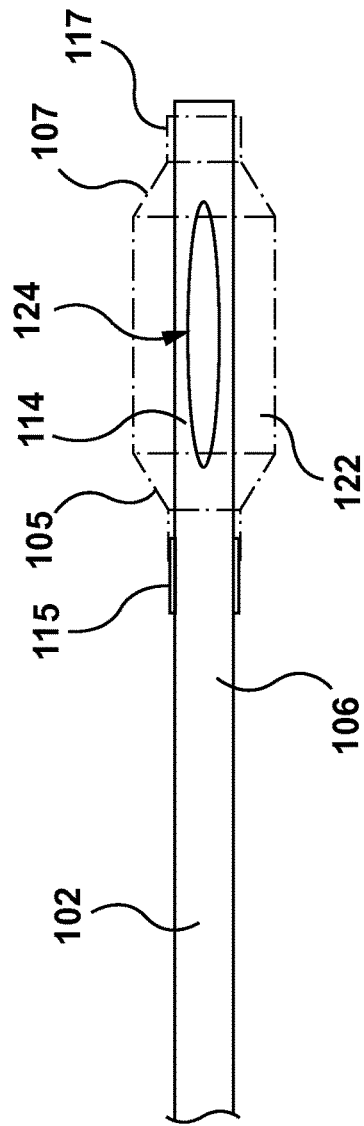
FIG. 4 is a schematic top view of the distal portion of the occlusion bypassing apparatus of FIG. 1 with the guidewires removed.
Figure 5:
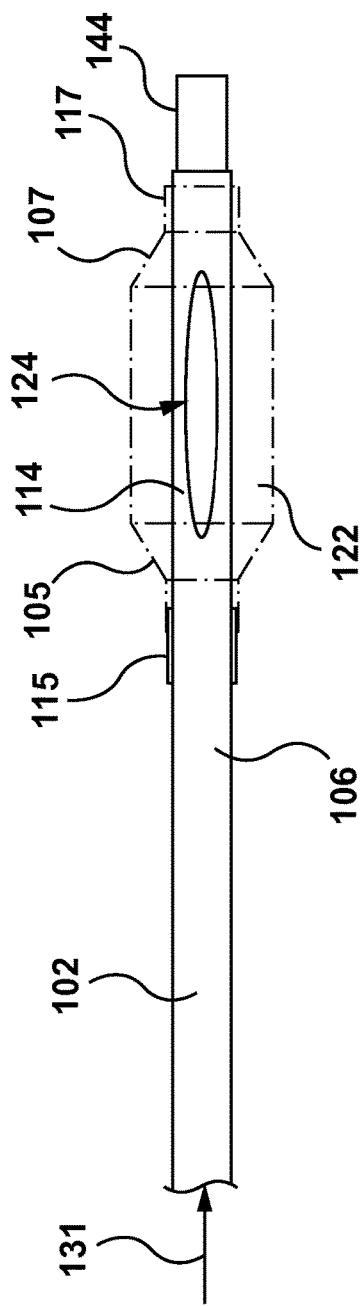
FIG. 5 is a schematic top view of the distal portion of the occlusion bypassing apparatus of FIG. 1 with a mandrel inserted therethrough to illustrate a manufacturing step of the lateral balloon.

Formation of balloon 122 will now be discussed with reference to FIG. 4 and FIG. 5. FIG. 4 is a schematic top view of the distal portion of the occlusion bypassing apparatus 100 with the guidewires removed. FIG. 5 is a schematic top view of the distal portion of the occlusion bypassing apparatus 100 with a mandrel 144 inserted therethrough to illustrate a manufacturing step of balloon 122. In order to form lateral chambers 122A, 122B, at least one weld 124 extends over body portion 130 of balloon 122. In an embodiment hereof, two welds 124 extend over opposing sides of body portion 130 of balloon 122 to form lateral chambers 122A, 122B thereof. Balloon 122 originates from a regular or known cylindrical balloon used for balloon angioplasty, i.e., a POBA or plain old balloon angioplasty balloon. When assembled over build-up tube 114, a single cylindrical POBA balloon is positioned over build-up tube 114 such that the balloon circumferentially surrounds build-up tube 114. The single cylindrical POBA balloon is laser welded to modify its shape to thereby form balloon 122. More particularly, as shown in FIG. 4, a fillet weld 124 is disposed over body portion 130 of balloon 122 to. Although not shown on the top view of FIG. 4, a second fillet weld 124 is disposed over the opposing side of body portion 130 as well. During the welding step, mandrel 144 may be positioned through lumen 112 of guidewire reinforcement component 110 and an inflation fluid (represented by directional arrow 131) is delivered as shown in FIG. 5. Fillet welds 124 create a flat or flattened balloon profile with the top and bottom opposing sides of balloon 122 being attached or constrained to build-up tube 114 while the left and right opposing sides of balloon 122 are not attached or constrained to build-up tube 114. In an embodiment, fillet welds 124 extend over the entire length of body portion 130 but do not extend over proximal and distal cones 105, 107, respectively. When inflated, the top and bottom sides of balloon 122 that are attached or constrained to build-up tube 114 remain fixed while the left and right sides of balloon 122 that are not attached or constrained to build-up tube 114 expand or inflate in opposing lateral directions away from build-up tube 114 to thereby form lateral chambers 122A, 122B. Lateral chambers 122A, 122B are in fluid communication with each other. When deflated, balloon 122 has a circular profile that conforms to build-up tube 114 for maneuvering occlusion bypassing apparatus 100 through a vasculature.

Figure 9:
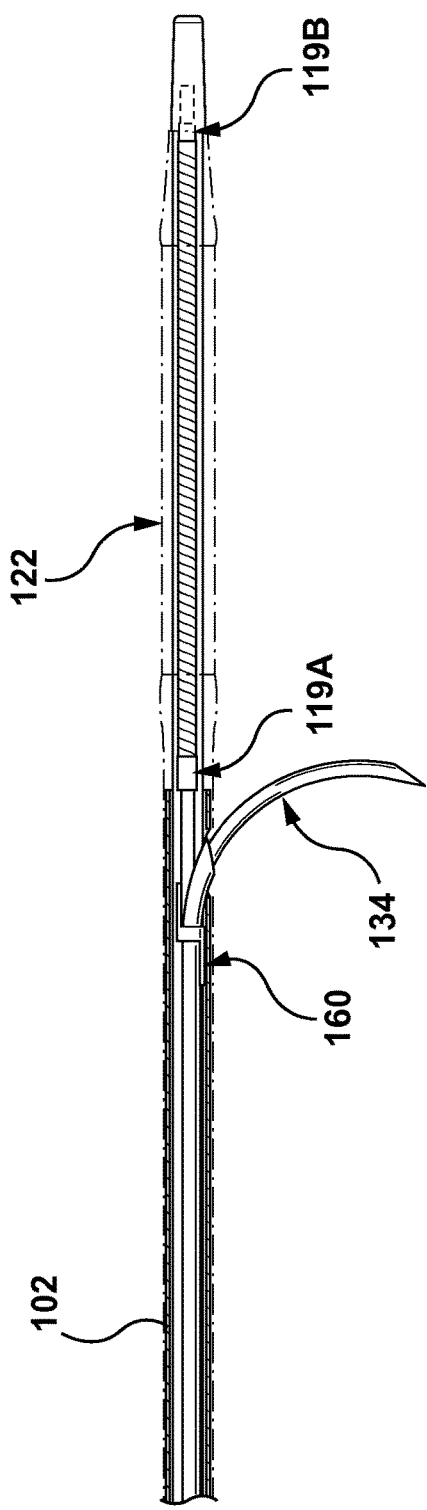
FIG. 9 is a side view of a distal portion of the occlusion bypassing apparatus of FIG. 1 with the guidewires removed, wherein the occlusion bypassing apparatus includes the radiopaque marker of FIG. 6.
Figure 10:
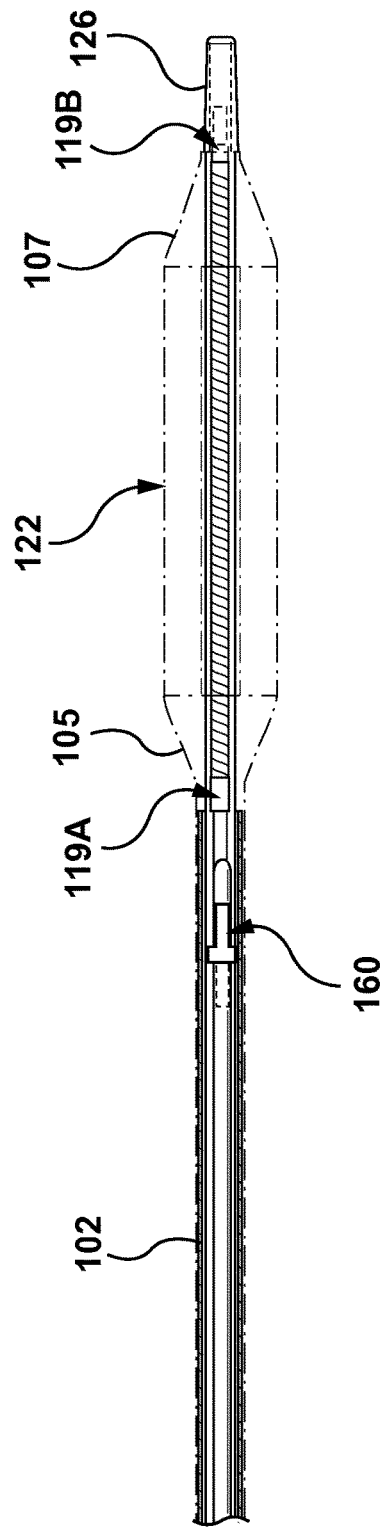
FIG. 10 is a top view of a distal portion of the occlusion bypassing apparatus of FIG. 1 with the guidewires removed, wherein the occlusion bypassing apparatus includes the radiopaque marker of FIG. 6.

Occlusion bypassing apparatus 100 may include radiopaque markers in order to visually monitor the location of the apparatus in situ as well as the orientation of the apparatus. Each marker has an individual function or advantage, and collectively, the relative positioning of the multiple markers may be utilized to detect device orientation. As shown in the exploded view of FIG. 3 as well as the side and top views of FIG. 9 and FIG. 10, respectively, cylindrical or ring first and second radiopaque markers 119A, 119B provide visibility of balloon 122 and thus assist in properly positioned the occlusion bypassing apparatus (balloon and outer shaft component are shown in phantom in FIGS. 9-10 so that the components internal thereto are clearly shown). Markers 119A, 119B may be coupled to an annular lumen of the occlusion bypassing apparatus, such as the guidewire lumen. For example, in an embodiment, markers 119A, 119 are positioned over guidewire reinforcement component 110 to mark or indicate body portion 130 of balloon 122. Markers 119A, 119B are positioned adjacent to proximal and distal cones 105, 107, respectively, of balloon 122. Markers 119A, 119B indicate or mark the proximal and distal ends of body portion 130 of the balloon in order to provide the user with information about balloon position. Marker 119B is also positioned adjacent to distal tip 126 of occlusion bypassing apparatus 100, and thus further provides visibility of the distal end of the apparatus during delivery and advancement thereof. Further, marker 119A functions to mark the maximum axial extension of the needle component when deployed. More particularly, marker 119A provides the user with information about the vessel portion that is potentially subject to contact the needle component when deployed.

Radiopaque marker 160, which may be considered a third radiopaque marker, allows a user to properly position occlusion bypassing apparatus 100 across an occlusion or lesion in situ and unequivocally identify the position of side port 108. FIG. 6 illustrates a perspective view of marker 160. Marker 160 is an asymmetrical, S-shaped radiopaque marker that may be coupled to a distal portion of a needle housing 116, which will be described in more detail herein. Marker 160 includes an annular or ring portion 180, a first leg portion 182, and a second leg portion 184. Leg portions 182, 184 extend from opposing sides of ring portion 180 and are 180 degrees offset from each other. As shown in the side and top views of FIG. 9 and FIG. 10, respectively, marker 160 has a unique and distinctive shape depending upon the orientation of the occlusion bypassing apparatus. Due to the unique and asymmetrical shape of marker 160, marker 160 allows a user to properly position the occlusion bypassing apparatus across an occlusion or lesion in situ and unequivocally identify the position and orientation of the side port. Collectively, the relative positioning of radiopaque markers 119A, 119B, 160 allow a user to identify or track the apparatus rotation across the lesion and proper needle orientation during deployment thereof. Further, markers 119A, 119B, 160 may be formed with different shapes, different dimensions, and/or different materials having different levels of radiopacity so that they may be distinguished from each other when in situ. Radiopaque markers 119A, 119B, 160 may be formed from Platinum-Iridium alloys, gold, tantalum, and/or loaded polymeric materials.

It will be understood by those of ordinary skill in the art that occlusion bypassing apparatuses described herein may utilize alternative radiopaque marker configurations and patterns in order to properly position the occlusion bypassing apparatus. For example, FIG. 7 illustrates another configuration of a radiopaque marker 760 that may be used in embodiments herein. Marker 760 may be coupled to a distal portion of needle housing 116. Marker 760 is generally T-shaped and includes an annular or ring portion 780, a first leg portion 782, and a second leg portion 784. Leg portions 782, 784 extend from opposing sides of ring portion 780 but are not circumferentially offset from each other. Due to its asymmetry, marker 760 has a unique and distinctive shape depending upon the orientation of the occlusion bypassing apparatus. Due to the unique shape of marker 760, marker 760 allows a user to properly position the occlusion bypassing apparatus across an occlusion or lesion in situ and unequivocally identify the position and orientation of the side port. Additional marker configurations may also be used in embodiments described herein, including but not limited to an L-shaped radiopaque marker 860 shown in FIG. 8. Marker 860 may be coupled to a distal portion of needle housing 116. Marker 860 includes an annular or ring portion 880 and a leg portion 882 extending from one end thereof. Due to its asymmetry, marker 860 has a unique and distinctive shape depending upon the orientation of the occlusion bypassing apparatus. Due to the unique shape of marker 860, marker 860 allows a user to properly position the occlusion bypassing apparatus across an occlusion or lesion in situ and unequivocally identify the position and orientation of the side port.

Needle lumen 109 of outer shaft component 102 houses needle housing 116. More particularly, needle housing 116 lays within needle lumen 109 of outer shaft component 102, or stated another way is disposed within a distal portion of needle lumen 109 of outer shaft component 102. Accordingly, with reference back to FIG. 1, FIG. 1A is a cross-sectional view taken along line A-A of FIG. 1 that shows needle component 134 within needle lumen 109, while FIG. 1B is a cross-sectional view taken along line B-B of FIG. 1 (which is taken at a more distal longitudinal location along occlusion bypassing apparatus 100) that shows needle component 134 within needle housing 116. Needle housing 116 is a tubular or cylindrical shaft component that is disposed at the distal portion of needle lumen 109, with a proximal end thereof (i.e., the two proximal-most tabs thereof) being embedded into the polymeric material of outer shaft component 102. Needle housing 116 defines a lumen sized and configured to slidably and removably receive needle component 134 there-through. When needle component 134 is positioned within occlusion bypassing apparatus 100, needle component 134 is disposed or extends through needle lumen 109 of outer shaft component 102 and through lumen 127 (see FIG. 1B) of needle housing 116.

In an embodiment hereof, needle housing 116 is a metallic tube of a relatively short length. Typically, the needle housing length is about 2-5% of the needle lumen length. Needle housing 116 is preferably formed from a shape memory material such as nitinol to ensure high flexibility of occlusion bypassing apparatus 100 during advancement through the vasculature. Alternatively, needle housing 116 may be formed from a metallic resilient material such as steel or spring temper stainless steel.

Figure 11:
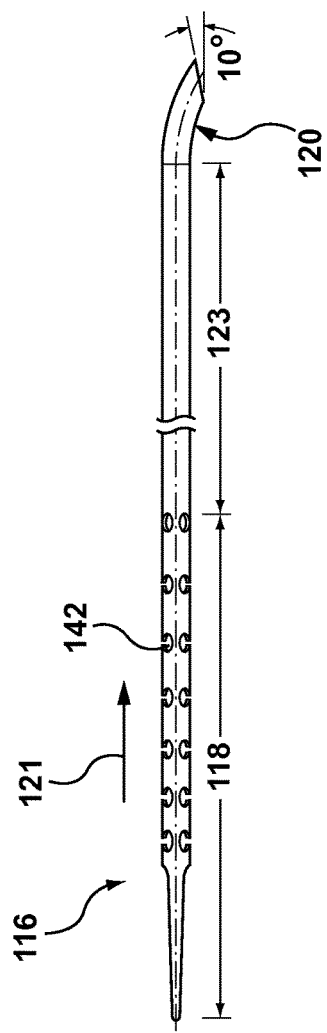
FIG. 11 is a side view of the needle housing of the occlusion bypassing apparatus of FIG. 1, wherein the needle housing is removed from the occlusion bypassing apparatus for illustrative purposes only.
Figure 12:
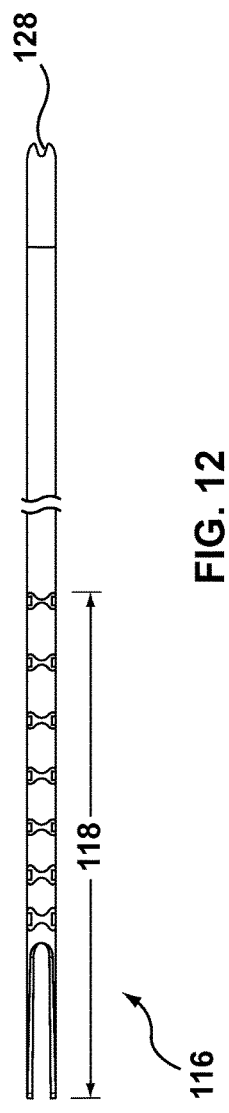
FIG. 12 is a top view of the needle housing of FIG. 11.

With reference to FIGS. 11-12, needle housing 116 includes a proximal transition portion 118 with a variable flexibility and a curved distal portion 120 that bends from the longitudinal axis $L_A$ of occlusion bypassing apparatus 100. FIG. 11 is a side view of needle housing 116, wherein the needle housing is removed from occlusion bypassing apparatus 100 for illustrative purposes only. FIG. 12 is a top view of needle housing 116. Curved distal portion 120 includes a pre-formed or pre-shaped bend or curve. A heat or thermal treatment of the selected material of needle housing 116 may be used to set the shape of curved distal portion 120. More particularly, as shown in FIG. 11, curved distal portion 120 extends, bends, or otherwise curves in a circular path while the remaining length of needle housing 116 is straight and extends parallel to the longitudinal axis $L_A$ of occlusion bypassing apparatus 100. In an embodiment hereof, curved distal portion 120 extends in a circular path and forms a portion of a circle having a radius R. In an embodiment hereof, radius R is 5 mm. Typically, radius R is in the range from 4 mm to 8 mm. As best shown in the sectional views of FIGS. 24 and 25, distal portion 120 of needle housing 116 terminates at side port 108 of outer shaft component 102. The curved distal portion 120 of needle housing 116 functions as a guide to direct needle component 134 through side port 108 such that needle component 134 exits occlusion bypassing apparatus 100 in a stable configuration at a desired orientation for re-entry into a true lumen. As shown in FIG. 11, in an embodiment, a distal end of curved distal portion 120 is angulated with respect to the longitudinal axis $L_A$ of occlusion bypassing apparatus 100. In FIG. 11, the distal end of curved portion 120 is angled at an angle of 10° with respect to the longitudinal axis $L_A$ of occlusion bypassing apparatus 100. In another embodiment hereof (not shown), a distal end of curved distal portion 120 is straight or parallel to the longitudinal axis $L_A$ of occlusion bypassing apparatus 100.

In order to smooth or bridge the transition between flexible needle lumen 109 and relatively stiffer or less flexible needle housing 116, needle housing 116 includes proximal transition portion 118. Transition portion 118 has a variable flexibility along its length that decreases in a distal direction as indicated by directional arrow 121 (see FIG. 11). Since the flexibility of transition portion 118 decreases in a distal direction, the transition portion allows for a gradual modulation of the flexibility between the flexible needle lumen 109 (located proximal to transition portion 118) and relatively less flexible, or rigid, remaining length of needle housing 116 (located distal to transition portion 118). The flexibility of occlusion bypassing apparatus 100 corresponds to the flexibility of needle housing 116, with occlusion bypassing apparatus 100 being more flexible proximal to needle housing 116 and less flexible along needle housing 116. Transition portion 118 similarly will provide occlusion bypassing apparatus 100 with a variable flexibility along its length that decreases in a distal direction.

In order to provide transition portion 118 of needle housing 116 with varying flexibility, transition portion 118 includes a plurality of apertures 142, wherein pairs of apertures align with each other along a respective transverse axis of needle housing 116. Each aperture is a cut-out portion or window that increases the flexibility of transition portion 118 as compared to the remaining length of needle housing 118, i.e., straightening portion 123 of needle housing 116 and curved distal portion 120 which have no apertures or cut-out portions formed therein. As used herein, any respective pair of aligned apertures may be referred to singularly or collectively as a pair or pairs of aligned apertures 142. Although shown with seven pairs of aligned apertures 142, a greater or lesser number of pairs of aligned apertures 142 may be used to provide transition portion 118 with varying flexibility. As further described in U.S. patent application Ser. No. 14/460,068 to Guala et al, filed Aug. 14, 2014, which is herein incorporated by reference in its entirety, each aperture in a pair of aligned apertures 142 has an hourglass shape and is disposed from the other aperture of the pair on an opposite side of the perimeter or outer surface of needle housing 116 so as to be diametrically opposed thereto. In order to provide transition portion 118 with varying flexibility along its length that decreases in a distal direction, the pitch or spacing between adjacent pairs of aligned apertures increases in a distal direction. The distance or spacing between adjacent pairs of aligned apertures 142 continues to increase such that distance or spacing between the most distal apertures is the greatest. Since a greater amount of metallic material extends between consecutive pairs of aligned apertures 142, gradually increasing the pitch or spacing between axially adjacent pairs of aligned apertures 142 in the distal direction results in a gradual decrease of flexibility in the distal direction. In addition or in the alternative to varying the spacing between adjacent pairs of aligned apertures 142, in another embodiment the size or area of adjacent pairs of aligned apertures 142 may be varied in order to result in a gradual decrease of flexibility along the length of transition portion 118 in the distal direction as further described in U.S. patent application Ser. No. 14/460,068 to Guala et al, filed Aug. 14, 2014, previously incorporated by reference.

Figure 13:
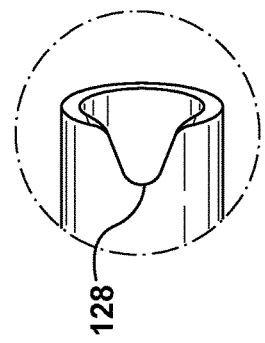
FIG. 13 is an enlarged perspective view of a distal tip of the needle housing of FIG. 11.

FIG. 13 is an enlarged perspective view of a distal tip of needle housing 116. More particularly, in order to improve embedding of needle housing 116 within outer shaft component 102, a small opening or skive cut 128 is formed at the very distal tip of curved distal end 120. Skive cut 128 grabs or embeds into the polymeric material of outer shaft component 102 and/or elongated proximal neck 115 of balloon 122 which encapsulates needle housing 116 within occlusion bypassing apparatus 100 to aid in securing needle housing 116 within outer shaft component 102.

Figure 14:
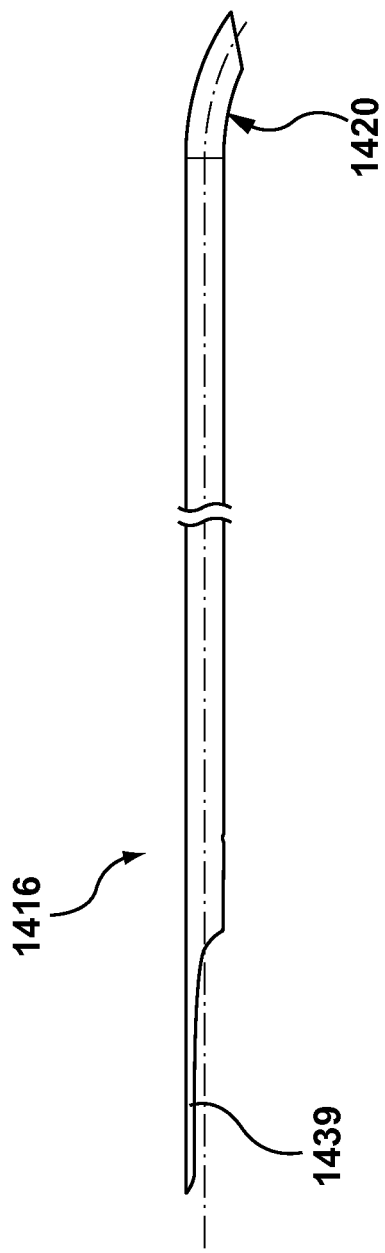
FIG. 14 is a side view of the needle housing of an occlusion bypassing apparatus according to another embodiment hereof, wherein the needle housing is removed from the occlusion bypassing apparatus for illustrative purposes only.
Figure 15:
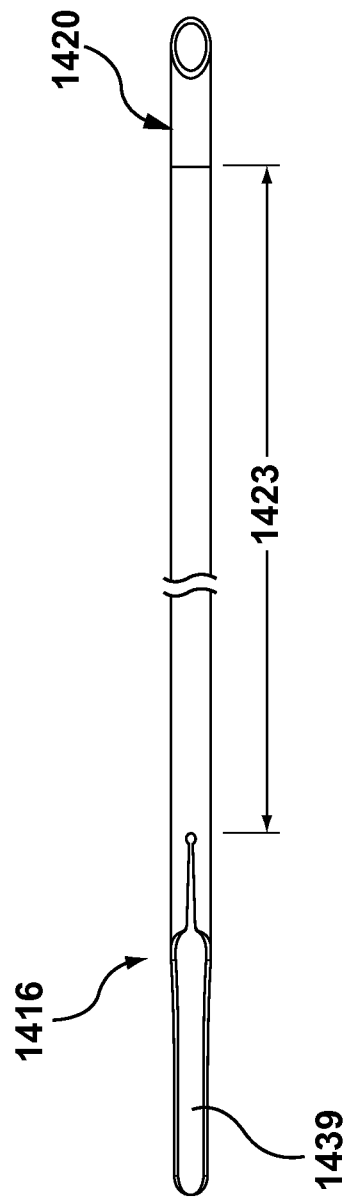
FIG. 15 is a top view of the needle housing of FIG. 14.

It will be understood by those of ordinary skill in the art that occlusion bypassing apparatuses described herein may utilize alternative needle housing configurations and patterns. More particularly, FIG. 14 is a side view of a needle housing 1416 according to another embodiment hereof, wherein the needle housing is removed from an occlusion bypassing apparatus for illustrative purposes only. FIG. 15 is a top view of needle housing 1416. Needle housing 1416 has a curved distal portion 1420 which is similar to curved distal portion 120. In order to provide needle housing 1416 with varying flexibility, a proximal portion of needle housing 1416 includes a tab 1439 formed by a skive cut which has a variable flexibility along its length that decreases in a distal direction. Further, tab 1439 is more flexible that the remaining length of needle housing 1416 i.e., straightening portion 1423 of needle housing 1416 and curved distal portion 1420 which have no cut-out portions formed therein. A width of tab 1418 increases along its length such that a distal end thereof is wider than a proximal end thereof. At least a portion of tab 1439 is configured to be embedded into the polymeric material of outer shaft component 102. In an embodiment, the entire length of tab 1439 is embedded into the polymeric material of outer shaft component 102. Further, tab 1439 provides proper orientation of the exit port of needle housing 1417 during assembly of the needle housing into the outer shaft component.

FIG. 16 is a side view of a needle housing 1616 according to another embodiment hereof, wherein the needle housing is removed from an occlusion bypassing apparatus for illustrative purposes only. FIG. 17 is a top view of needle housing 1616. Needle housing 1616 has a curved distal portion 1620 which is similar to curved distal portion 120. In order to provide needle housing 1616 with varying flexibility, a proximal portion of needle housing 1616 includes an expandable stent 1618 which is more flexible that the remaining length of needle housing 1616 i.e., straightening portion 1623 of needle housing 116 and curved distal portion 1620 which have no apertures or cut-out portions formed therein. Stent 1618 is self-expanding and is configured to expand into apposition with the polymeric material of outer shaft component 102. More particularly, stent 1618 is a tubular frame or scaffold that defines a plurality of diamond or kite-shaped openings, with each diamond-shaped opening being defined by four vertexes or vertices and four segments or struts extending or formed between vertexes. In this embodiment, stent 1618 has a lattice or mesh configuration which is laser cut from a tube and is formed as a unitary structure or component. In embodiments hereof, stent 1618 may be made from stainless steel, a pseudo-elastic metal such as a nickel titanium alloy or Nitinol, or a so-called super alloy, which may have a base metal of nickel, cobalt, chromium, or other metal.

Figure 45:
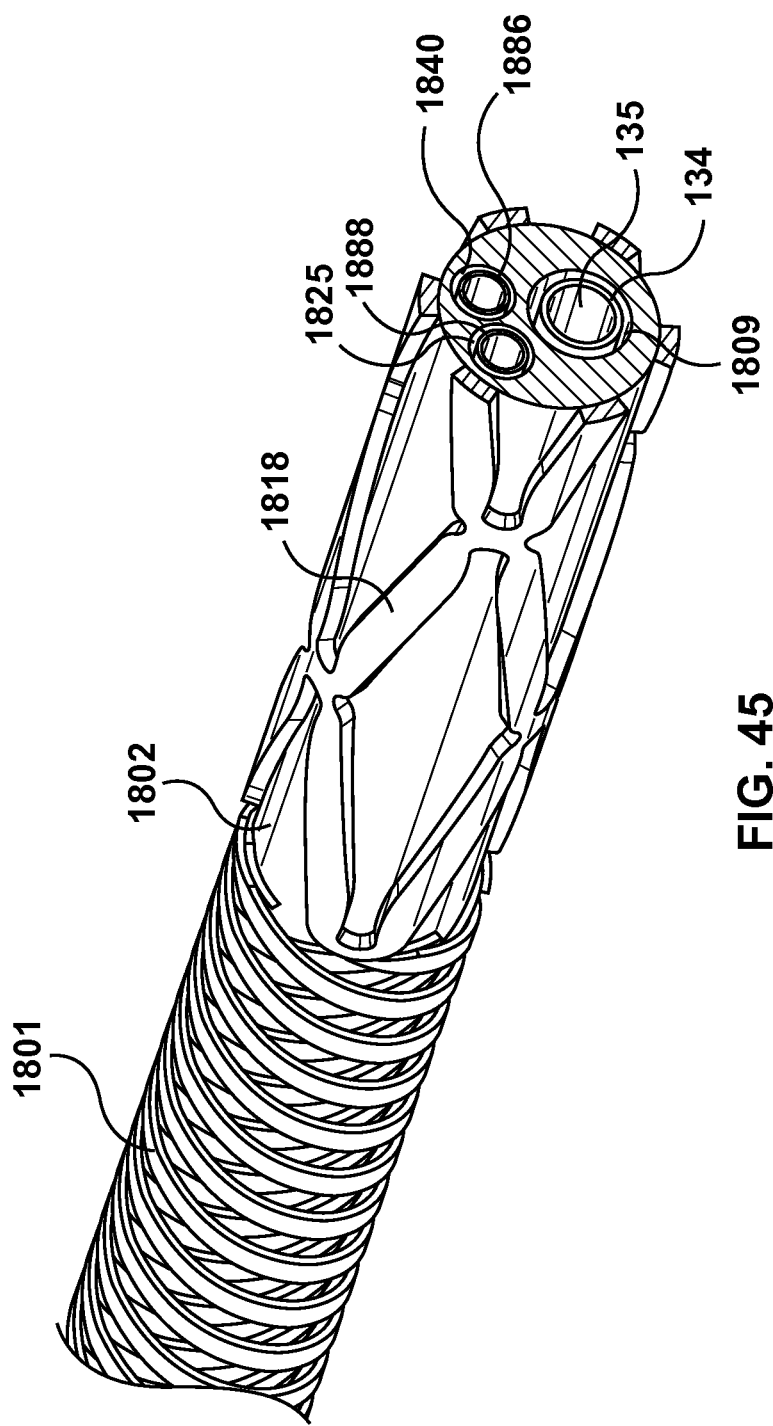
FIG. 45 is a perspective view of a portion of the needle housing of FIGS. 18-19 and the outer shaft component, terminating at a transition portion of the needle housing to illustrate a cross-sectional view thereof, wherein a polymeric outer or external jacket of the outer shaft component is not shown for clarity purposes only.

FIG. 18 is a side view of a needle housing 1816 according to another embodiment hereof, wherein the needle housing is removed from an occlusion bypassing apparatus for illustrative purposes only. FIG. 19 is a top view of needle housing 1816. Needle housing 1816 has a curved distal portion 1820 which is similar to curved distal portion 120. In order to provide needle housing 1816 with varying flexibility, a proximal portion of needle housing 1816 includes an expandable stent 1818 which is more flexible that the remaining length of needle housing 1816 i.e., straightening portion 1823 of needle housing 1816 and curved distal portion 1820 which have no apertures or cut-out portions formed therein. Stent 1818 is a tubular frame or scaffold that defines a plurality of diamond or kite-shaped openings, with each diamond-shaped opening being defined by four vertexes or vertices and four segments or struts extending or formed between vertexes. In this embodiment, stent 1818 has a lattice or mesh configuration which is laser cut from a tube and is formed as a unitary structure or component. Stent 1818 is self-expanding and may be made from stainless steel, a pseudo-elastic metal such as a nickel titanium alloy or Nitinol, or a so-called super alloy, which may have a base metal of nickel, cobalt, chromium, or other metal. However, rather than being configured to expand into apposition with the polymeric material of the outer shaft component as described with respect to stent 1618, stent 1818 is sized and configured to embrace or surround an outer surface of the outer shaft component. More particularly, as shown in FIGS. 44, 44A, and 45, stent 1818 becomes the distal end of a braided or reinforcement layer 1801 disposed over an outer shaft component 1802 and a polymeric external jacket (such as external jacket 103 described herein but not shown in FIGS. 44, 44A, and 45 for purposes of clarity) is over-molded onto stent 1818 to secure or attach stent 1818 and needle housing 1816 to outer shaft component 1802. The remaining length of needle housing 1816, i.e., straightening portion 1823 of needle housing 1816 and curved distal portion 1820 which have no apertures or cut-out portions formed aligns with a needle lumen 1809 of outer shaft component 1802 so stent 1818 is eccentric with respect to straightening portion 1823 of needle housing 1816 and curved distal portion 1820. As shown in FIGS. 44, 44A, and 45, needle component 134 (which defines lumen 135 for receiving reentry guidewire 170 as described herein) is slidingly disposed through aligned needle lumen 1809 of outer shaft component 1802 and the remaining length of needle housing 1816, i.e., straightening portion 1823 of needle housing 1816 and curved distal portion 1820. In this embodiment, a distal end 1806 of outer shaft component 1802 terminates within stent 1818 and thus the occlusion bypassing system includes a first connection shaft 1886 which extends within a distal portion of a guidewire lumen 1840 and distally extends beyond distal end 1806 of outer shaft component 1802 to bridge or connect the guidewire lumen of the outer shaft component to a guidewire reinforcement component (such as guidewire reinforcement component 110 described herein but not shown in FIGS. 44, 44A, and 45) and a second connection shaft 1888 which extends within a distal portion of an inflation lumen 1825 and distally extends beyond distal end 1806 of outer shaft component 1802 to bridge or connect the inflation lumen of the outer shaft component to the inlet or interior of a balloon (such as balloon 122 described herein but not shown in FIGS. 44, 44A, and 45). First and second connection shafts 1886, 1888 may be formed of poli-imide or other suitable polymeric materials.

Figure 20:
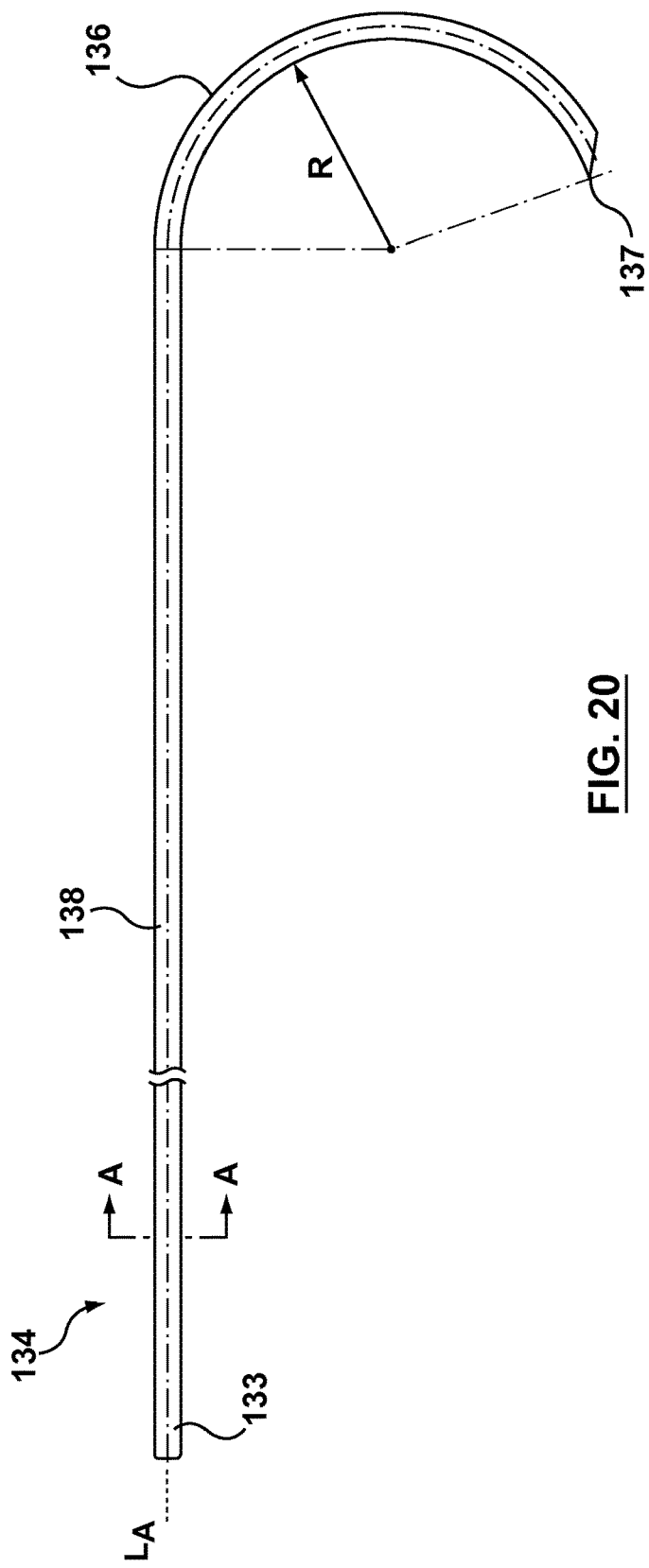
FIG. 20 is a side view of the needle component of the occlusion bypassing apparatus of FIG. 1, wherein the needle component is removed from the occlusion bypassing apparatus for illustrative purposes.
Figure 20A:
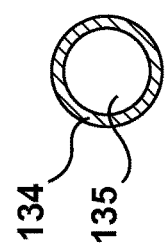
FIG. 20A is a cross-sectional view of the needle component of FIG. 20 taken along line A-A thereof.

Needle component 134, which is shown removed from occlusion bypassing apparatus 100 in FIG. 20, is a tubular or cylindrical element that is configured to be slidably disposed within lumens 109, 127 of outer shaft component 102, needle housing 116, respectively, and removable therefrom. More particularly, needle component 134 is disposed within outer shaft component 102 and needle housing 116 such that there is sufficient space or room there-between for needle component 134 to be movable or slidable in a longitudinal direction relative to outer shaft component 102 and needle housing 116. In order to accommodate reentry guidewire 170 that may be utilized during a method of subintimally crossing an occlusion as will be discussed in more detail herein, needle component 134 may be a hypotube that defines a lumen 135 there-through as shown in the cross-sectional view of FIG. 20A. In an embodiment, lumen 135 of needle component 134 is sized to accommodate a guidewire having an outer diameter equal to or less than 0.014 inch such that occlusion bypassing apparatus 100 has a low profile. A proximal end of needle component 134 is housed within handle 151 and distal tip 137 of needle component 134 is configured to pierce or penetrate through a wall of a vessel when extended or deployed.

Needle component 134 includes an elongated first or proximal segment 138 that extends substantially parallel with longitudinal axis $L_A$ of occlusion bypassing apparatus 100 and curved distal end 136 distally extending from a distal end of proximal segment 138. Curved distal end 136 is pre-formed in a bent or curved shape or configuration. More particularly, as shown in FIG. 20, curved distal end 136 extends, bends, or otherwise curves in a circular path. In an embodiment hereof, curved distal end 136 extends in a circular path approximately 160° from a distal end of proximal segment 138, thereby forming a portion of a circle having a radius R. "Approximately" as used herein includes angles with a plus or minus 20° error margin. In an embodiment hereof, radius R is 5 mm. At least curved distal end 136 of needle component 134 is formed from a biocompatible resilient metal such as spring temper stainless steel or nitinol, which utilizes the elastic properties of stress induced martensite, such that a heat or thermal treatment of the selected material may be used to set the shape of curved distal end 136. In an embodiment, needle component 134 may be formed from more than one material, for e.g., with proximal segment 138 being formed of stainless steel and only curved distal end 136 being formed of nitinol. With additional reference to FIG. 25, curved distal portion 120 of needle housing 116 is formed with the same curvature as curved distal end 136 of needle component 134 so that an automatic centering design is obtained. More particularly, curved distal portion 120 of needle housing 116 includes a bend or turn that corresponds with, matches or is the same as the bend or turn of curved distal end 136 of needle component 134. The bend of curved distal portion 120 of needle housing 116 is formed with the same radius R as the bend of curved distal end 136 of needle component 134 so that the needle component 134 exits side port 108 of outer shaft component 102 at or with the correct orientation for re-entry of a true lumen of a vessel. By forming curved distal portion 120 of needle housing 116 and curved distal end 136 of needle component 134 with identical curvatures or radiuses, needle component 134 is very stable inside needle housing 116, thus minimizing any rotation or relative movement between the two components, especially during the needle deployment.

In another embodiment hereof, the needle component may include a straight segment disposed between the curved distal end and the distal tip. More particularly, FIG. 21 is a side view of a distal portion of a needle component 2134 according to another embodiment hereof, wherein the needle component includes a straight segment 2145 disposed between curved distal end 2136 and distal tip 2137. Straight segment 2145 may range between 1 and 3 mm in length, and functions to improve the angulation of reentry guidewire 170 into the vessel true lumen. Stated another way, straight segment 2145 improves the direction of reentry guidewire 170 so that reentry guidewire 170 exits from needle component 134 and is directed distal of the occlusion rather than being directed backward toward the occlusion.

In addition, the needle component may include a radiopaque marker to improve visibility thereof and allow a user to visually check and then correctly track the deployment of the needle component. For example, FIG. 22 is a side view of a distal portion of a needle component 2234 according to another embodiment hereof, wherein the needle component includes an encapsulated radiopaque marker 2243 proximal to distal tip 2237 thereof. In an embodiment, marker 2243 is a small gold pill can be inserted within a recess formed on an outer surface of needle component 2234. As another example, FIG. 23 is a side view of a distal portion of a needle component 2334 according to another embodiment hereof, wherein the needle component includes a curved distal portion 2336 and a distal tip 2337, wherein distal tip 2337 and a portion of distal portion 2336 is coated in a radiopaque coating 2343. Radiopaque coating 2343 is a thin layer of material and may be formed by sputtering, dipping, or other suitable process.

With reference now to FIG. 24, in a first or delivery configuration of the apparatus the curved distal end 136 of needle component 134 is held or restrained in a straightened form within needle housing 116. Balloon 122 and inflation lumen 125 are not shown in FIG. 24 since the sectional view is taken approximately through the midline of occlusion bypassing apparatus 100 and proximal to distal end 106 of outer shaft component 102. Needle housing 116 is formed from a relatively stiff or less flexible material as described above in order to effectively straighten curved distal end 136 of needle component 134. More particularly, in an embodiment hereof, needle component 134 is pre-loaded within occlusion bypassing apparatus 100 and curved distal end 136 of needle component 134 is held or restrained in a straightened form within straightening portion 123 of needle housing 116 which has no apertures or cut-out portions formed therein. Since needle housing 116 is formed with varying flexibility, straightening portion 123 of needle housing 116 with no apertures or cut-out portions is relatively stiffer or less flexible to ensure straightening of curved distal end 136 of needle component 134. Straightening portion 123 of needle housing 116 holds the curved distal end of the needle component in a straightened form during advancement of occlusion bypassing apparatus 100 in the human vasculature.

In the sectional view of FIG. 25, curved distal end 136 of needle component 134 extends from side port 108 of outer shaft component 102 and bends or curves from longitudinal axis $L_A$ of the apparatus. Balloon 122 and inflation lumen 125 are not shown in FIG. 24 since the sectional view is taken approximately through the midline of occlusion bypassing apparatus 100 and proximal to distal end 106 of outer shaft component 102. More particularly, when it is desired to distally advance needle component 134 through side port 108 of outer shaft component 102, it must first be confirmed that side port 108 is positioned beyond or distal to the target occlusion and is oriented in the direction of the true lumen of the vessel. The position and orientation of occlusion bypassing apparatus may be monitored via radiopaque markers 119A, 119B, 160 of apparatus 100 described above. Once side port 108 is positioned and oriented as desired, needle component 134 is distally advanced relative to outer shaft component 102 such that curved distal end 136 is no longer constrained by needle housing 116 but rather is extended to protrude from side port 108 of outer shaft component 102. When released from needle housing 116, curved distal end 136 resumes its pre-formed shape or geometry by its own internal restoring forces. As described with respect to FIG. 20, curved distal end 136 extends, bends, or otherwise curves in a circular path, thereby forming a portion of a circle having a radius R. When needle component 134 is distally advanced or extended as best shown in FIGS. 1, 2, and 25, distal tip 137 may be used to penetrate through the vessel wall and re-enter a true lumen of a vessel as described herein. As described above, by forming the bend of curved distal end 136 of needle component 134 with the same curvature or radius as the bend of curved distal portion 120 of needle housing 116, deployed needle component 134 is very stable inside needle housing 116, thus minimizing any rotation or relative movement between the two components. Balloon 122 may be expanded or inflated to anchor outer shaft component 102 within a subintimal tract either before or after the distal advancement of needle component 134. In an alternative method of the present invention, according to the physician's experience during the procedure he may realize that the subintimal space is sufficiently narrow and suitably envelops the occlusion bypassing apparatus that the latter is properly anchored within the subintimal space. Therefore, in this case there could be no need for expanding the balloon.

Figure 26:
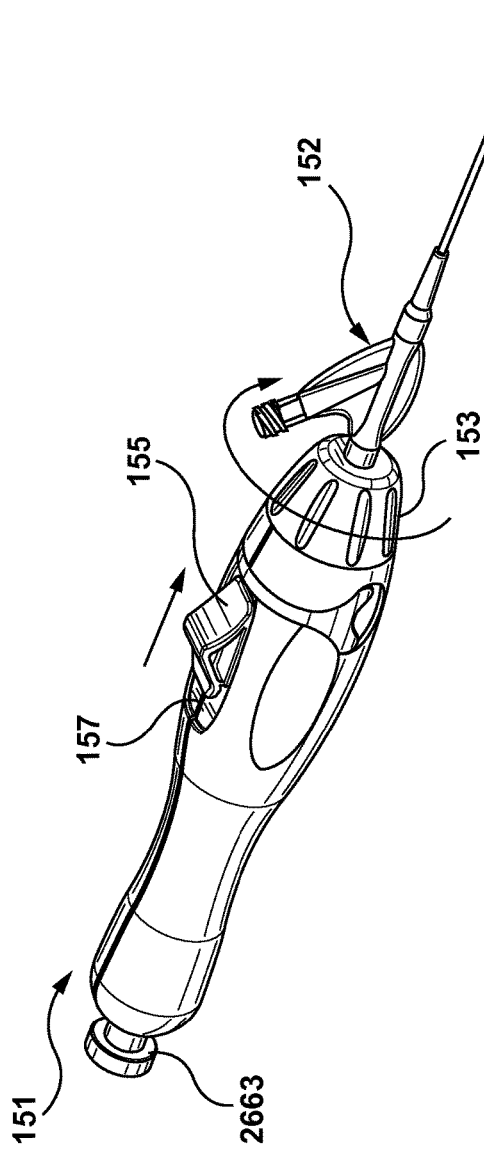
FIG. 26 is a perspective view of the handle of the occlusion bypassing apparatus of FIG. 1 with the guidewires removed.
Figure 27:
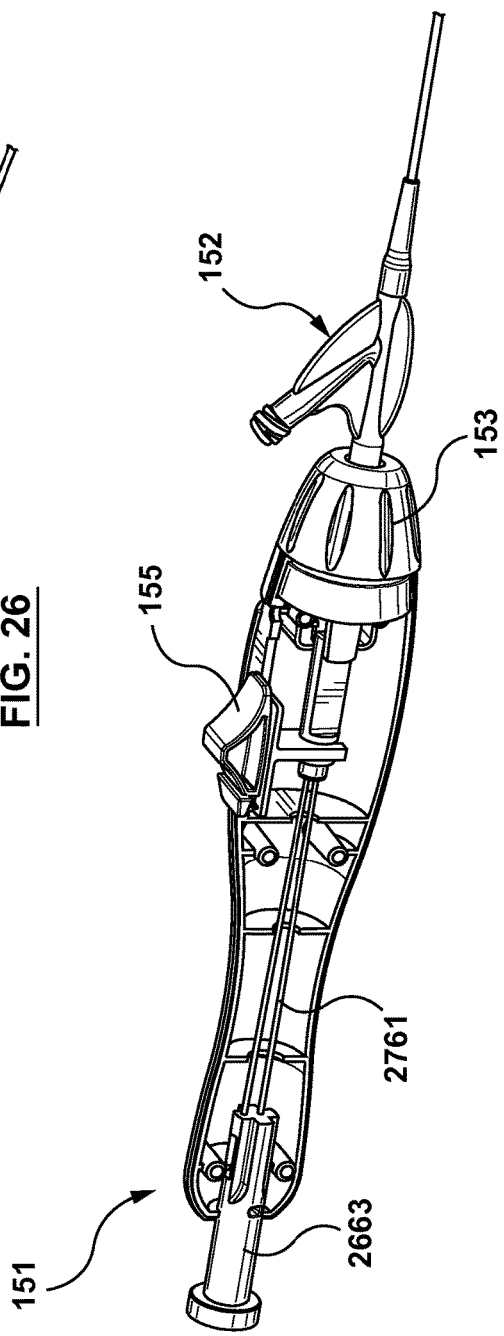
FIG. 27 is a sectional perspective view of the handle of the occlusion bypassing apparatus of FIG. 1 with the guidewires removed.

Occlusion bypassing apparatus 100 may have handle 151 coupled thereto in order to assist in the manipulation of needle component 134 and outer shaft component 102. As shown in FIG. 1 and FIGS. 26-27, handle 151 includes a knob or cogwheel 153 and a slider 155. FIG. 26 is a perspective view of handle 151 with guidewires 140, 170 removed, while FIG. 27 is a sectional perspective view of handle 151 with guidewires 140, 170 removed. Hub 152, previously described herein, extends between knob 153 and outer shaft component 102. Knob 153 is coupled to outer shaft component 102 such that rotation of the knob results in rotation of the outer shaft, as well as any components attached thereto or incorporated therein such as needle housing 116. More particularly, if a user needs to rotate outer shaft component 102 in order to orient side port 108 towards a true lumen of a vessel, the user turns knob 153 to manipulate outer shaft component 102 as desired. Slider 155 is attached to needle component 134 such that operation of slider 155 results in deployment or retrieval of the needle component. More particularly, when it is desired to deploy or retrieve needle component 134, slider 155 is pushed or pulled within a recess 157 formed on handle 151. Handle 151 also includes a tubular component 2761 (shown in FIG. 27) that houses needle component 134 within the handle in order to prevent kinking of the needle component. Further, handle 151 also includes a flushing luer 2663 (shown in FIG. 26) so that occlusion bypassing apparatus 100 may be flushed prior to use within the vasculature in accordance with techniques known in the field of interventional cardiology and/or interventional radiology. Flushing of occlusion bypassing apparatus 100 is described in more detail herein.

Figure 29:
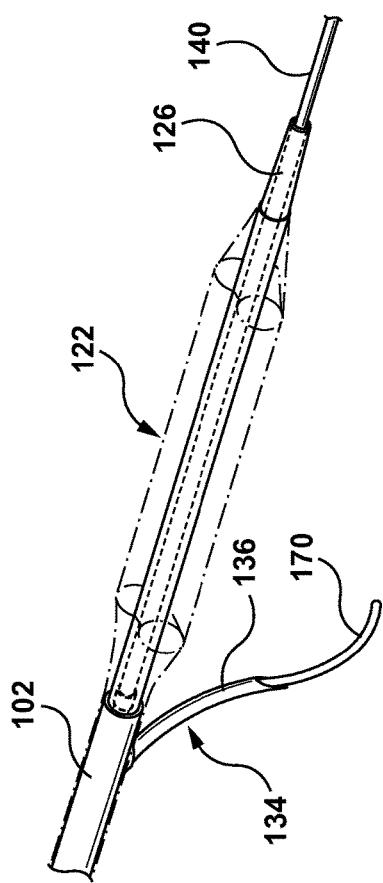
FIG. 29 is an enlarged perspective view of the distal portion of the occlusion bypassing apparatus of FIG. 1.
Figure 30:
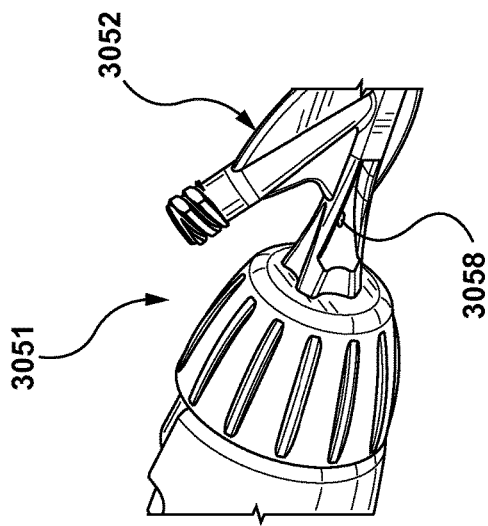
FIG. 30 is an enlarged perspective view of a luer that may be utilized in embodiments hereof, wherein the luer has an exit port formed therein.
Figure 28:
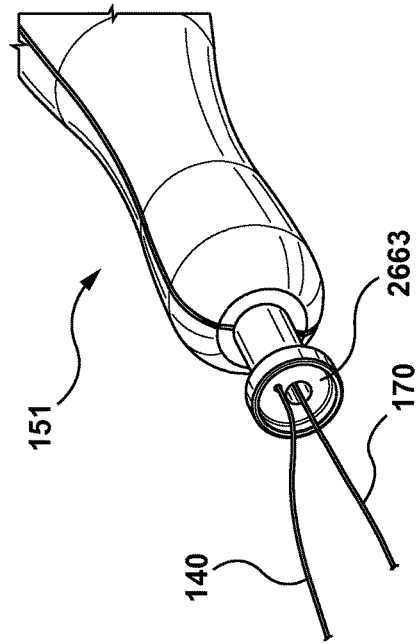
FIG. 28 is an enlarged perspective view of a proximal end of the handle of the occlusion bypassing apparatus of FIG. 1.

FIG. 28 is an enlarged perspective view of a proximal end of handle 151, while FIG. 29 is an enlarged perspective view of the distal portion of the occlusion bypassing apparatus 100. As best shown on FIG. 28, flushing luer 1663 is configured to permit exit of both tracking guidewire 140 and reentry guidewire 170 from the proximal end of handle 151. As shown on FIG. 29, tracking guidewire 140 exits from distal tip 126 of occlusion bypassing apparatus 100 while reentry guidewire 170 exits from distal tip 137 of needle component 134. In another embodiment hereof, the flushing luer may be configured to only permit exit of reentry guidewire 170 and tracking guidewire 140 may exit distal to handle 151. For example, FIG. 30 is an enlarged perspective view of a hub 3052 that may be utilized in embodiments hereof, wherein the hub has an exit port 3058 formed therein. In this embodiment, tracking guidewire 140 used to track occlusion bypassing apparatus 100 through the vasculature is intended to exit before handle 3051. Exit port 3058 is a dedicated recess drawn within hub 3052 which bridges or extends between handle 3051 and the outer shaft component (not shown in FIG. 30).

Figure 31:
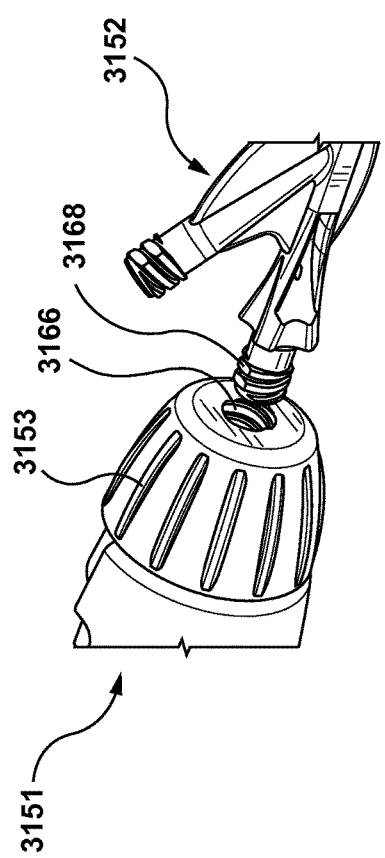
FIG. 31 is an enlarged perspective view of a luer that may be utilized in embodiments hereof, wherein the luer may be disengaged or disconnected from the handle.

The handle may incorporate various additional features. For example, FIG. 31 is an enlarged perspective view of a hub 3152 that includes a bail-out feature so that the hub may be disengaged or disconnected from the handle. Such a bail-out feature may be useful where, for any reasons, the handle and/or the apparatus fails such as but not limited to when retraction of needle component 134 cannot be accomplished. More particularly, handle 3151 allows detachment of hub 3152 that bridges or extends between handle 3151 and the outer shaft component (not shown in FIG. 31). Hub 3152 includes threads 3168 that mate with helical recesses 3166 formed within a knob 3153 of handle 3151 to allow for separation or detachment of handle 3151 from occlusion bypassing apparatus 100. When handle 3151 is manually separated or detached from occlusion bypassing apparatus 100, needle component 134 is concurrently retracted within outer shaft component 102 since the needle component 134 is attached to the flushing luer at the proximal end of the handle (not shown on FIG. 31). In this case, when a bail-out is required, the user pulls back handle 3151 with one hand while keeping the other hand over hub 3152 to detach or separate handle 3151, and needle component 134 is thereby retracted within outer shaft component 102. FIG. 31 illustrates handle 3151 while separating from hub 3152. Although shown as being detachably coupled via threads, handle 3151 may be detachably coupled to hub 1352 via other coupling features like detachable bonds or adhesives.

Figure 32:
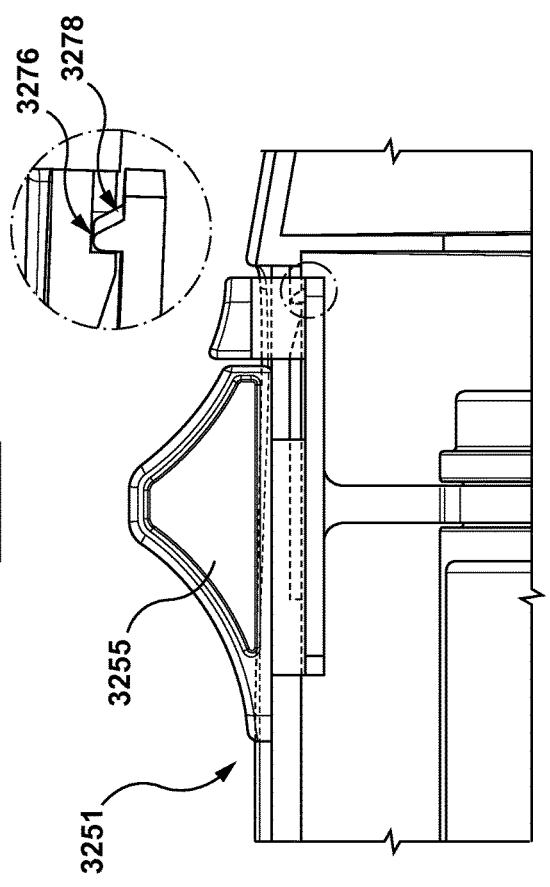
FIG. 32 is a side sectional view of a slider that may be utilized in embodiments hereof, wherein the slider includes a built-in safety mechanism.

FIG. 32 is a side sectional view of a slider 3255 that may be utilized in embodiments hereof, wherein the slider includes a built-in safety mechanism. Moreover, handle 3251 includes a safety blockage of slider 3255 to prevent unintended needle deployment while tracking through the vasculature. Slider 3255 includes a radial extension or tab 3278 on an underside surface thereof that engages or is received into a recess 3276 formed on a housing or shell of handle 3251. Tab 3278 secures slider 3255 in a locked position until the user exerts a force onto slider 3255 to disengage tab 3278 from recess 3276 when deployment of needle component 134 is desired.

FIGS. 33-34 illustrate another handle feature that may be utilized in embodiments hereof. More particularly, handle 3351 is configured to permit a two-stage needle deployment if desired. Handle 3351 includes a removable stopper 3390 built into the housing or shell of handle 3351. Stopper 3351 is shown positioned on handle 3351 in FIG. 33, thus resulting in standard needle deployment depth, and stopper 3351 is shown removed from handle 3351 in FIG. 34, thus resulting in additional or extra needle deployment depth. Stopper 3390 is loaded or positioned onto handle 3351 during assembly or packaging of the apparatus. When stopper 3390 is positioned on handle 3351 as shown in FIG. 33, occlusion bypassing apparatus 100 is configured for a standard needle deployment depth of approximately 5-6 mm. When stopper 3390 is removed as shown in FIG. 34, slider 3355 and needle component 134 may be further distally advanced and thus occlusion bypassing apparatus 100 is configured for an extra 3 mm needle deployment depth such that the total needle deployment depth is 8-9 mm. The extra needle deployment depth may be desirable depending upon application. For example, occlusion bypassing apparatus 100 may be designed or configured for treatment within a peripheral vasculature for use in SFA and Popliteal arteries. However, since from proximal SFA to distal popliteal the trunk size of the artery narrows down of some millimeters, the extra 3 mm needle deployment depth is designed to cover this gap. Stopper 3390 may be removed after needle component 134 is deployed the standard deployment depth and it is determined that additional or extra depth is desired. Stopper 3390 thus permits either a single-step needle deployment when the standard deployment depth is sufficient (and thus stopper 3390 is not required to be removed), or a two-step needle deployment when additional or extra depth is desired (and thus stopper 3390 is removed following the first step of needle deployment to the standard deployment depth).

Figure 35:
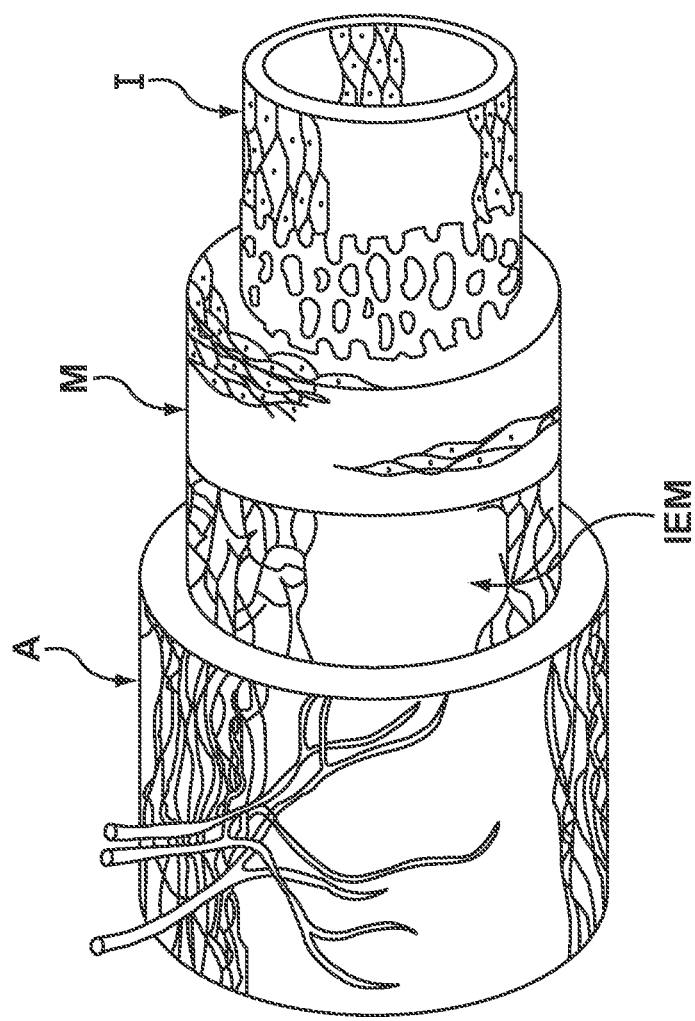
FIG. 35 is a diagram of an artery showing the three layers of tissue that comprise the artery wall.

FIG. 35 is a sectional view of the anatomy of an artery wall, which for purposes of this description is shown to consist essentially of three layers, the tunica intima I ("intima"), tunica media M ("media") which is the thickest layer of the wall, and the tunica adventitia A ("adventitia"). In some arteries an internal elastic membrane IEM is disposed between the media M and adventitia A. The adventitia A is made of collagen, vasa vasorum and nerve cells, the media M is made of smooth muscle cells, and the intima I is made up of a single layer of endothelial cells that provide a nonthrombogenic surface for flowing blood. Occlusion bypassing apparatus 100 is used as part of a system for creating a subintimal reentry tract within a wall of a blood vessel V to allow blood flow around an occlusion. FIGS. 36-43 illustrate an exemplary method of using the above-described occlusion bypassing apparatus 100 to bypass a chronic total occlusion (CTO) according to an embodiment hereof. Although described in relation to bypassing a CTO, it should be understood that the methods and apparatus described herein may be used for bypassing any tight stenoses in arteries or other anatomical conduits and are not limited to total occlusions.

Prior to use of occlusion bypassing apparatus 100 within the vasculature, it may be desirable to flush the apparatus in accordance with techniques known in the field of interventional cardiology and/or interventional radiology. Flushing of occlusion bypassing apparatus 100 may be performed through lumen 135 of needle component 134. More particularly, small openings or holes (not shown) may be provided on needle component 134. In order to perform the initial flushing of occlusion bypassing apparatus 100, side port 108 of outer shaft component 102 is occluded. Saline solution is introduced into a proximal end of lumen 135 of needle component 134 and flushes lumen 135. Since side port 108 is occluded, the saline solution exits from the small holes formed on needle component 134 and flushes needle lumen 109 of outer shaft component and lumen 127 of needle housing 116.

Figure 36:
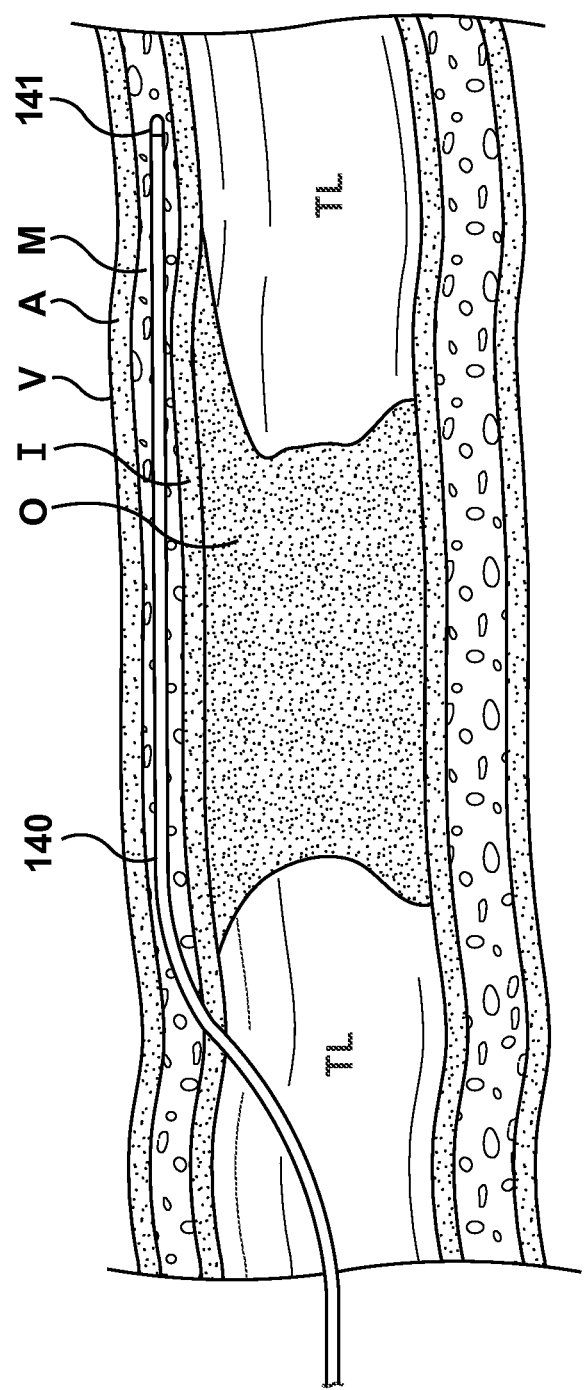
FIG. 36 illustrates a step of a method of crossing an occlusion within a vessel, wherein a guidewire has been transluminally advanced through the vasculature to a position upstream of a treatment site, which in this instance is shown as occlusion O within a true lumen TL of blood vessel V.

As shown in FIG. 36, in accordance with techniques known in the field of interventional cardiology and/or interventional radiology, tracking guidewire 140 having a distal end 141 is transluminally advanced through the vasculature to a position upstream of a treatment site, which in this instance is shown as occlusion O within a true lumen TL of blood vessel V. Tracking guidewire 140 pierces the intima I and is advanced distally to create a subintimal tract by locally dissecting or delaminating intima I from media M or by burrowing through media M. In order to pierce the intima I, a clinician may manipulate distal end 141 of tracking guidewire 140 by prolapsing or bending-over the distal end of tracking guidewire 140 (not shown) and thereafter may use the stiffer arc or loop of the prolapsed distal end to pierce into the intima I to advance tracking guidewire 140 there through. The piercing of the intima I is aided by the fact that typically blood vessel V is diseased, which in some instances makes the intima I prone to piercing. Tracking guidewire 140 is distally advanced within the subintimal tract from a near side of occlusion O to a position where distal end 141 thereof is positioned in the subintimal tract on a far side of occlusion O.

Alternatively, another device other than tracking guidewire 140 initially may be used to create the subintimal tract. Those of ordinary skill in the art will appreciate and understand the types of alternative devices that may be used in this step including an apparatus known as an "olive", a laser wire, an elongate radiofrequency electrode, a microcatheter, or any other device suitable for boring or advancing through the vessel tissue. As another example, a guidewire other than tracking guidewire 140 may be utilized to create the subintimal tract. More particularly, a guidewire having a relatively larger outer diameter than tracking guidewire 140, such as between 0.032-0.040 inches, may be utilized to create the subintimal tract because a larger guidewire has greater column strength to gain access to the subintimal space of vessel V. If an alternative device is used instead of tracking guidewire 140 to form the subintimal tract, such alternative device may be removed and replaced with tracking guidewire 140 after the subintimal tract has been formed.

Figure 37:
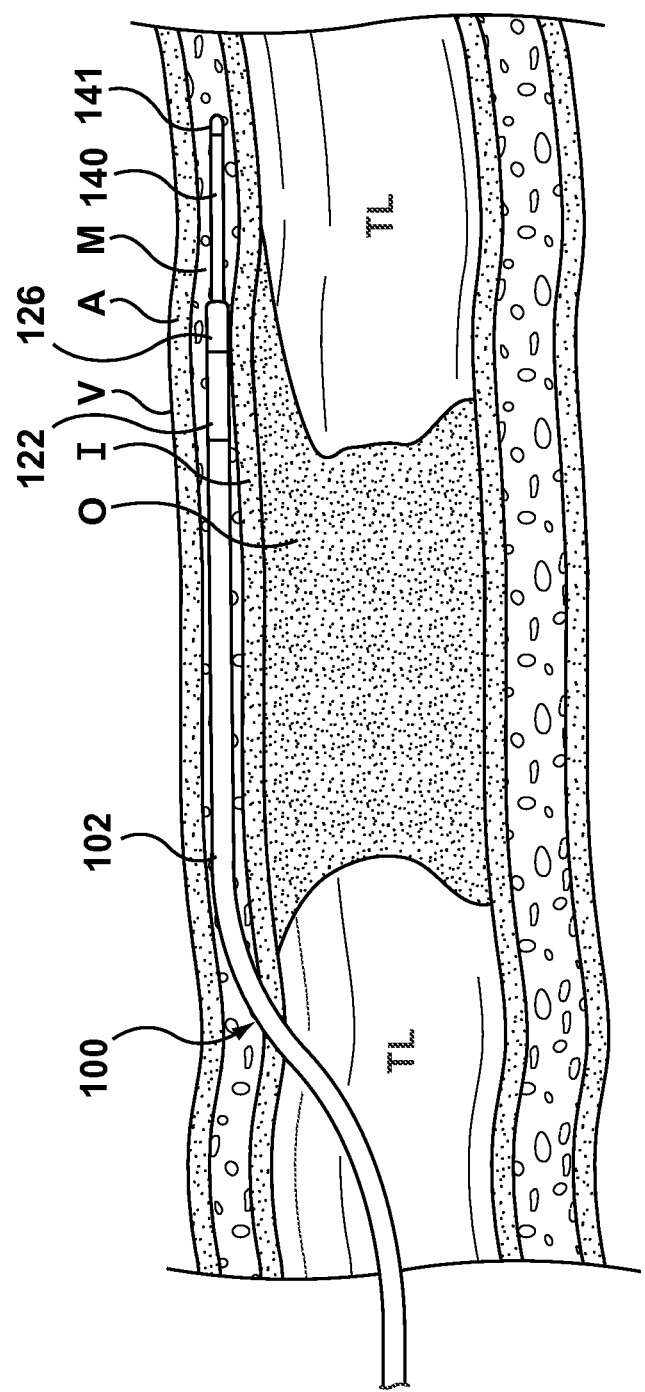
FIG. 37 illustrates another step of a method of crossing an occlusion within a vessel, wherein the occlusion bypassing apparatus of FIG. 1 is tracked over the guidewire.

After the subintimal tract is formed and guidewire 140 is in place as desired, occlusion bypassing apparatus 100 may be tracked over guidewire 140 and advanced such that distal tip 126 is adjacent to the far or downstream end of occlusion O as shown in FIG. 37. In an embodiment, needle component 134 is pre-loaded within occlusion bypassing apparatus 100. During the step of advancing occlusion bypassing apparatus 100 over guidewire 140, curved distal end 136 of needle component 134 is held or restrained in a straightened form within needle housing 116 as described above. In another embodiment, needle component 134 is not positioned or disposed within occlusion bypassing apparatus 100 when occlusion bypassing apparatus 100 is initially advanced over guidewire 140 but rather is subsequently introduced into the apparatus. Utilizing the radiopaque markers of apparatus 100, occlusion bypassing apparatus 100 should be positioned and oriented such that side port 108 of outer shaft component 102 is positioned beyond or distal to the target occlusion and is oriented in the direction of the true lumen of the vessel.

Figure 38:
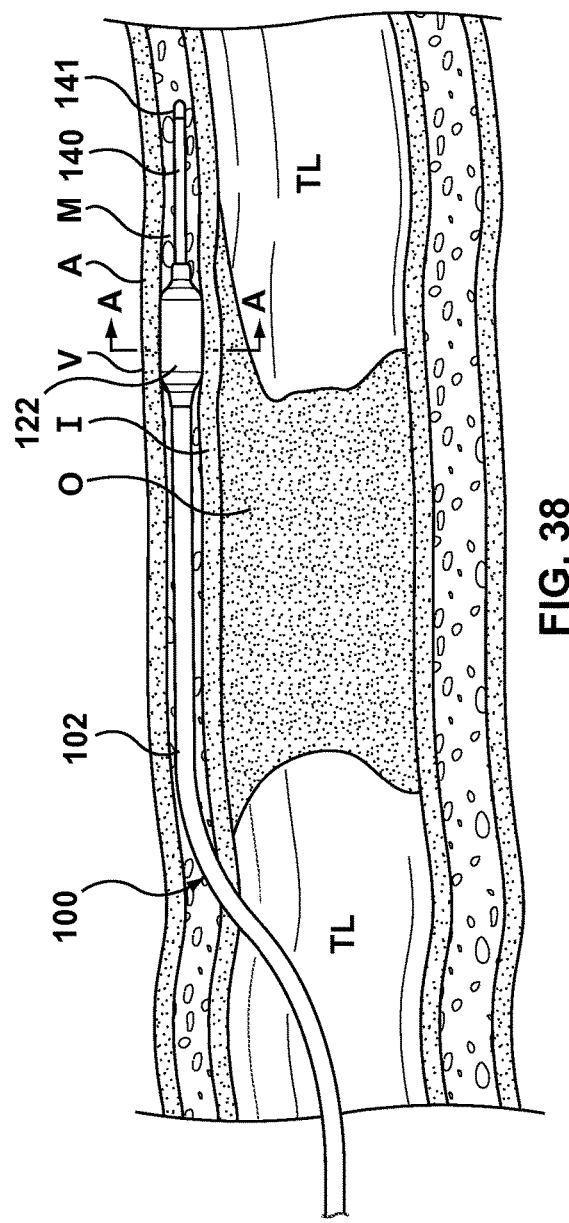
FIG. 38 illustrates another step of a method of crossing an occlusion within a vessel, wherein a balloon of the occlusion bypassing apparatus is inflated to anchor the apparatus within the subintimal space.
Figure 38A:
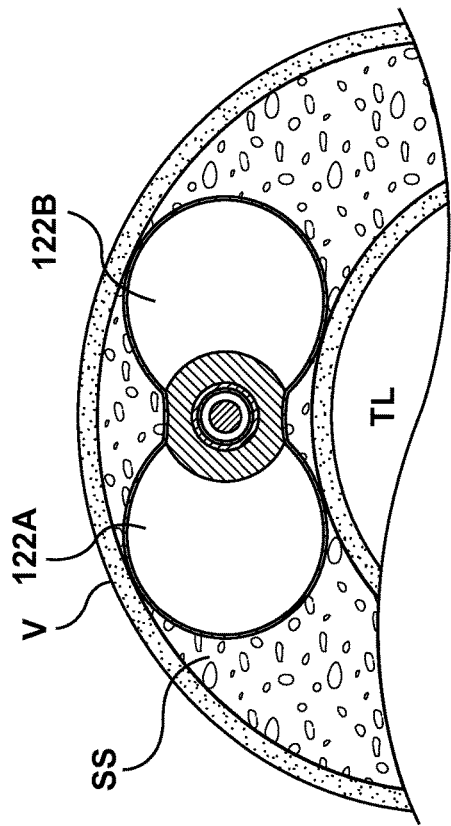
FIG. 38A is a cross-sectional view of a portion of the vessel of FIG. 38, taken along line A-A of FIG. 38.

Once outer shaft component 102 is positioned as desired, balloon 122 may be expanded or inflated as shown in FIG. 38 and FIG. 38A, thus anchoring outer shaft component 102 in the subintimal tract. FIG. 38A illustrates a cross-sectional view of apparatus 100 within a vessel V having a true lumen TL and a subintimal space SS. The subintimal space SS may be described as having an arc, curve, or C shape. When inflated, lateral chambers 122A, 122B of balloon 122 expand into contact with the surrounding patient's anatomy to fill out or occupy the subintimal space SS to improve anchoring and to minimize damage to the surrounding anatomy. In addition, although balloon 122 is described herein for providing stabilization during distal advancement or deployment of needle component 134, in another embodiment hereof (not shown) inflation of balloon 122 may also be used to create or assist in creating the subintimal tract. In such an embodiment, balloon 122 may be inflated multiple times in the subintima to initially support delivery of the occlusion bypassing apparatus across the lesion within the subintima and then subsequently during a re-entry procedure.

Figure 39:
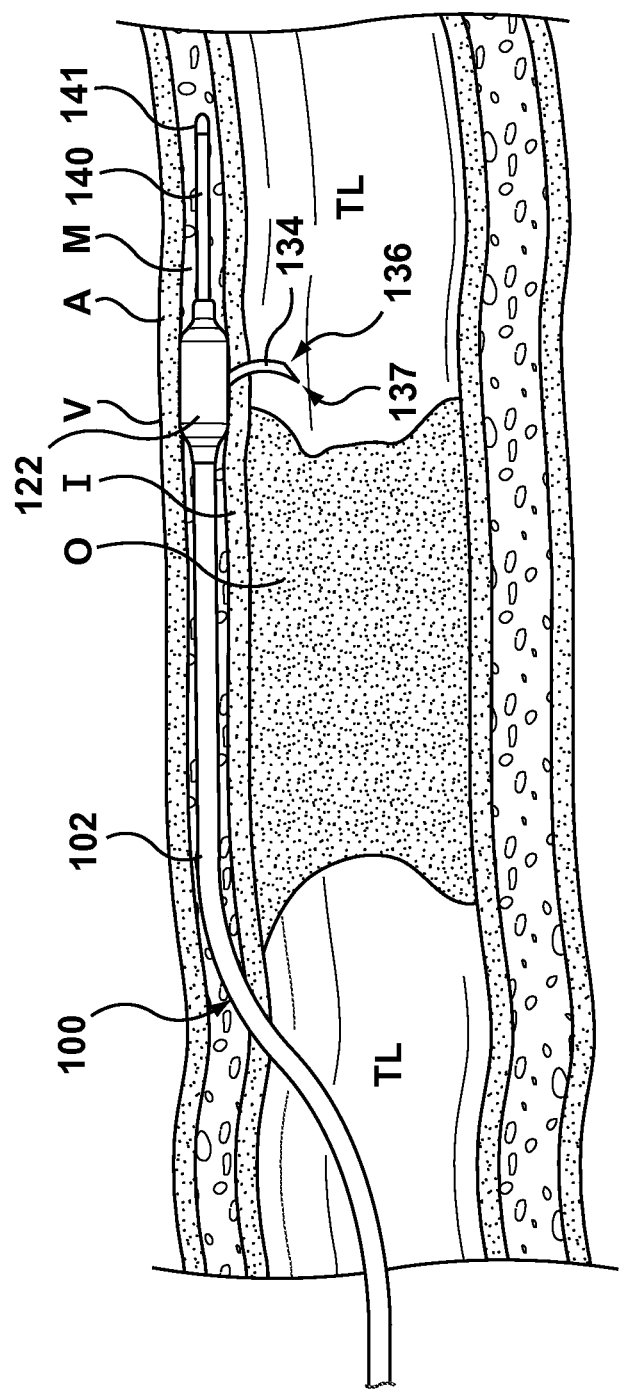
FIG. 39 illustrates another step of a method of crossing an occlusion within a vessel, wherein a needle component of the occlusion bypassing apparatus is distally advanced and deployed out of a side port of the outer shaft component.

With reference to FIG. 39, needle component 134 is then deployed through side port 108 of occlusion bypassing apparatus 100. Needle component 134 is distally advanced relative to outer shaft component 102 and needle housing 116 until curved distal end 136 extends from or protrudes out of side port 108 of outer shaft component 102 such that distal tip 137 of the needle component penetrates the intima to gain access to the true lumen of the vessel distal to, i.e., downstream of, the CTO. More particularly, needle component 134 is distally advanced relative to outer shaft component 102 (as well as needle housing 116 housed within outer shaft component 102) such that curved distal end 136 is no longer constrained by needle housing 116 but rather is extended to protrude from side port 108 of outer shaft component 102. When released from needle housing 116, curved distal end 136 resumes its pre-formed shape or geometry by its own internal restoring forces. As described with respect to FIG. 20, curved distal end 136 extends, bends, or otherwise curves in a circular path, thereby forming a portion of a circle having a radius R. When needle component 134 is distally advanced or extended as in FIG. 39, distal tip 137 may be used to penetrate through the vessel wall and re-enter a true lumen of a vessel. As described above, by forming the bend of curved distal end 136 of needle component 134 with the same curvature or radius as the bend of curved distal portion 120 of needle housing 116, deployed needle component 134 is very stable inside needle housing 116, thus minimizing any rotation or relative movement between the two components.

Figure 40:
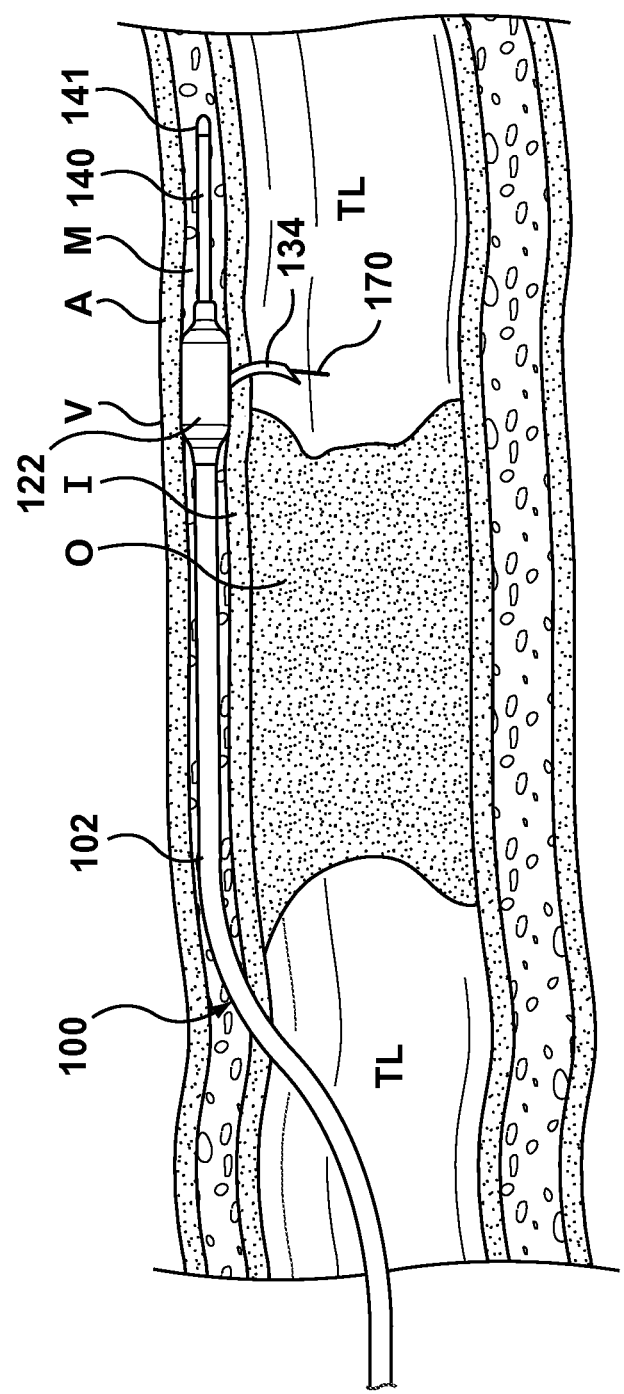
FIG. 40 illustrates another step of a method of crossing an occlusion within a vessel, wherein a second guidewire is advanced through the deployed needle component.
Figure 41:
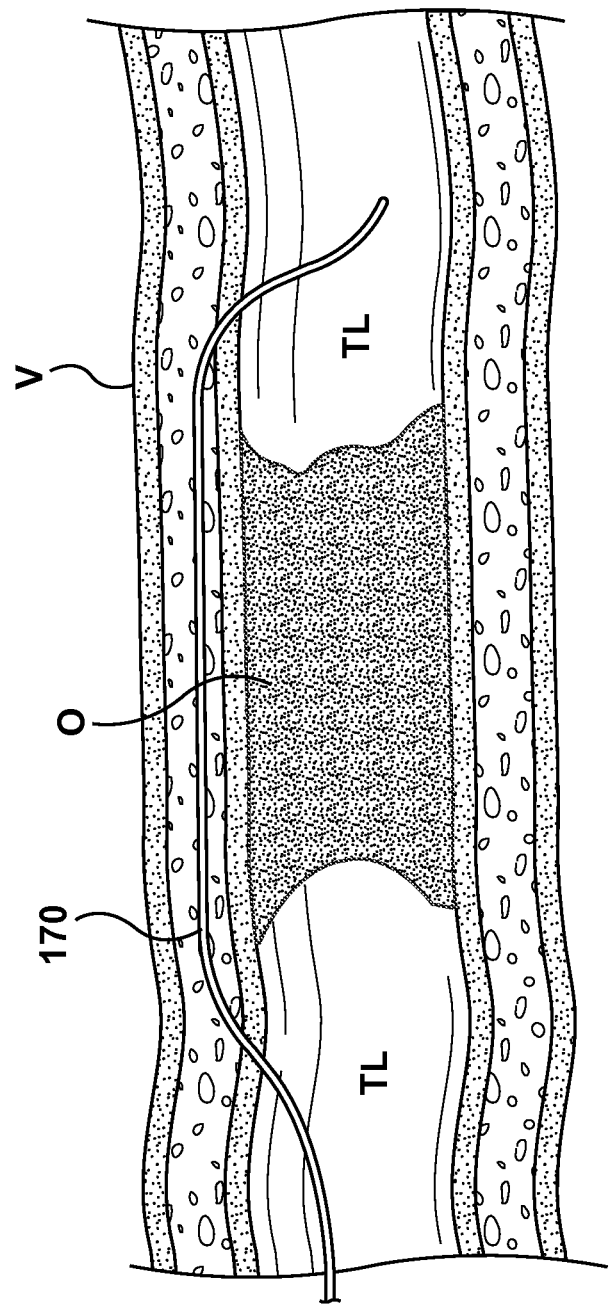
FIG. 41 illustrates another step of a method of crossing an occlusion within a vessel, wherein the occlusion bypassing apparatus is retracted and removed, leaving only the second guidewire in place.

Reentry guidewire 170 may be advanced through lumen 135 of needle component 134 and into the true lumen TL of vessel V as shown in FIG. 40. Reentry guidewire 170 has a relatively smaller outer diameter such as 0.014 inches in order to minimize the size of needle component 134 and subsequently, minimize the size of occlusion bypassing apparatus 100. Additionally, occlusion bypassing apparatus 100 may be removed and reentry guidewire 170 may be left in place as shown in FIG. 41, with reentry guidewire 170 extending in true lumen TL proximal to the CTO, through the subintimal tract, and back into true lumen TL distal to the CTO such that the CTO may now be successfully crossed via the pathway or conduit thus created.

Figure 42:
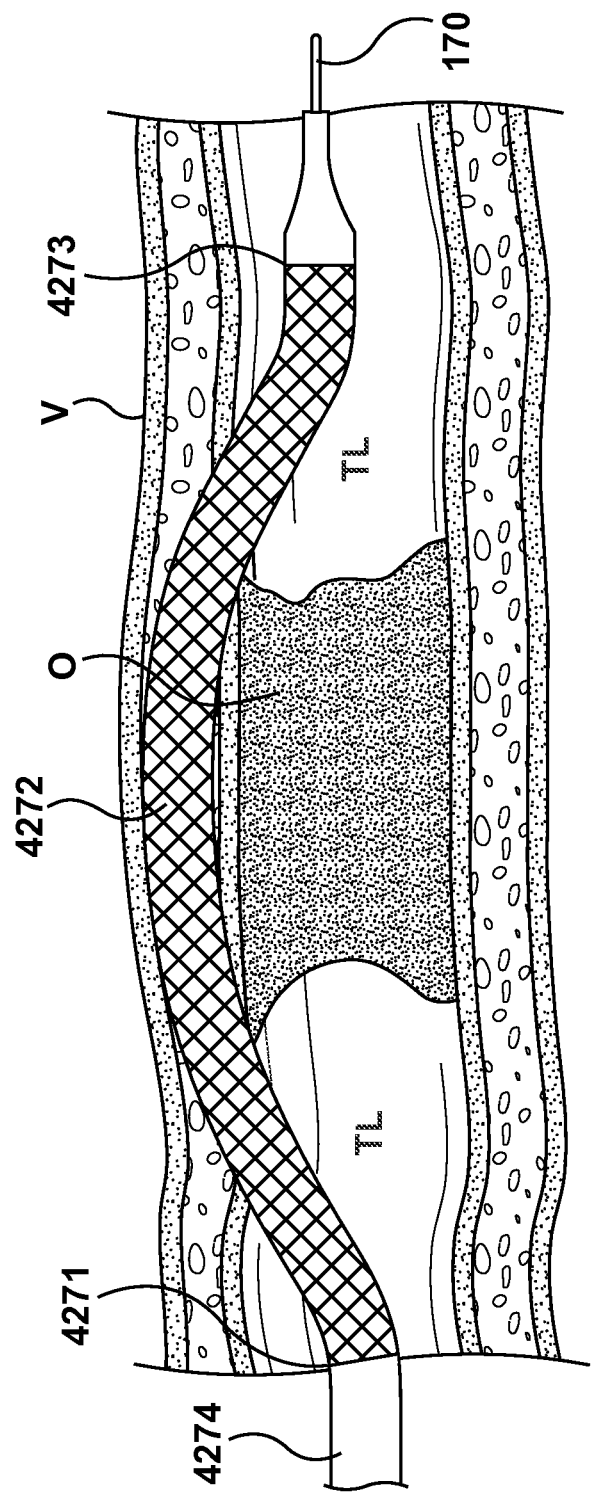
FIG. 42 illustrates another step of a method of crossing an occlusion within a vessel, wherein a stent delivery catheter is tracked over the second guidewire and the stent is expanded.
Figure 43:
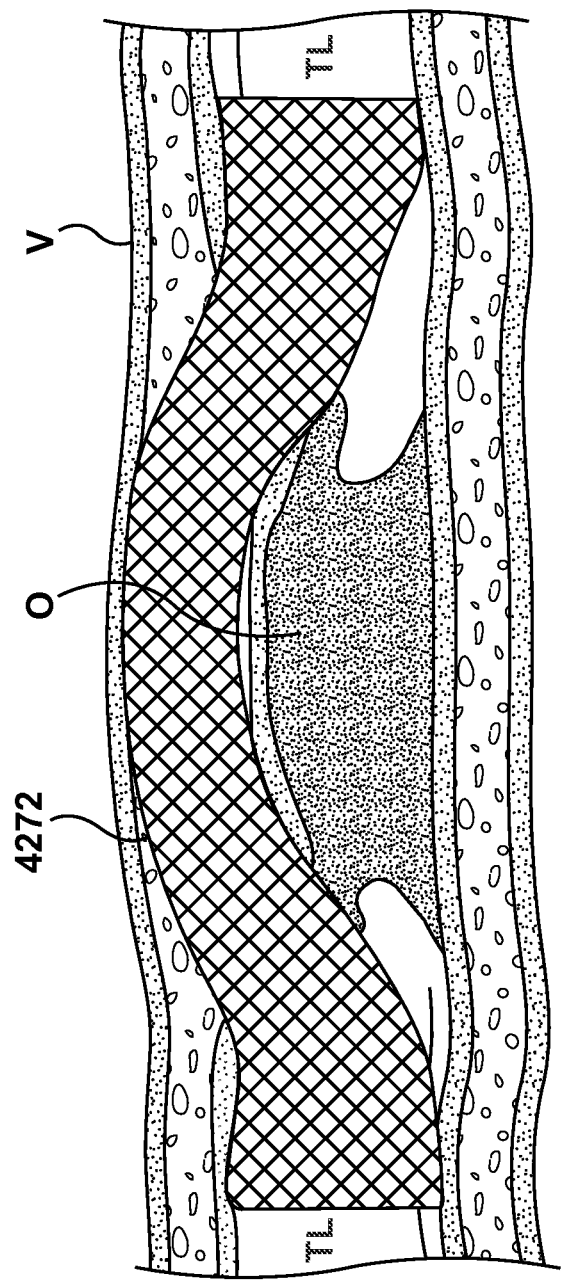
FIG. 43 illustrates another step of a method of crossing an occlusion within a vessel, wherein the stent delivery catheter and second guidewire are refracted and removed, leaving only the expanded stent in place.

Additionally, a covered or uncovered stent may be delivered over reentry guidewire 170 and implanted within the subintimal tract to facilitate flow from the lumen of the vessel upstream of the CTO, through the subintimal tract and back into the lumen of the vessel downstream of the CTO. FIG. 42 shows a distal end of a catheter 4274 having a stent 4272 mounted thereon being advanced over reentry guidewire 170 to a position where a distal end 4273 of the radially collapsed stent 4272 is in true lumen TL of vessel V downstream of chronic total occlusion CTO, a proximal end 4271 of stent 4272 is in true lumen TL of vessel V upstream of chronic total occlusion CTO, and a tubular body of stent 4272 extends through the subintimal tract. Stent 4272 is then deployed by either self-expansion or balloon inflation within the subintimal reentry tract to dilate the subintimal tract and compress the adjacent chronic total occlusion CTO. Stent 4272 provides a scaffold which maintains the subintimal tract in an open condition capable of carrying blood downstream of chronic total occlusion CTO. Thereafter, reentry guidewire 170 and catheter 4274 may be removed from the patient, leaving stent 4272 in an expanded configuration and creating a radially supported, subintimal blood flow channel around chronic total occlusion CTO as seen in FIG. 43. In some cases, it may be desirable to enlarge the diameter of the subintimal tract before advancing stent catheter 4274 into and through it. Such enlargement of the subintimal tract may be accomplished by passing a balloon catheter over reentry guidewire 170 and inflating the balloon to dilate the tract, or may be any other suitable tract enlarging, dilating or debulking instrument that may be passed over reentry guidewire 170.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An apparatus for bypassing an occlusion in a blood vessel comprising:
    an outer shaft component having a side port proximal to a distal end thereof, the outer shaft component including a needle lumen there-through that includes a curved distal portion that bends from a longitudinal axis of the apparatus and terminates at the side port of the outer shaft component and an inflation lumen there-through configured to receive inflation fluid;
    a needle housing formed from a tubular shaft and disposed within the outer shaft component, the needle housing including a curved distal portion that defines the curved distal portion of the needle lumen and a transition proximal portion that has a variable flexibility along its length that decreases in a distal direction;

a needle component configured to be slidably disposed within the needle lumen of the outer shaft component and removable therefrom; and an inflatable balloon disposed at the distal end of the outer shaft component and in fluid communication with the inflation lumen of the outer shaft component, the balloon including a body portion that is disposed distal to the side port of the outer shaft component, the body portion of the balloon having a flattened profile in an inflated state with first and second chambers that laterally extend from opposing sides of the outer shaft component for stabilizing the apparatus within a subintimal space.

2. The apparatus of claim 1, wherein the body portion of the balloon has a circular profile in a deflated state for maneuvering the apparatus through a vasculature.

3. The apparatus of claim 1, wherein at least one weld extends over the body portion of the balloon to form the first and second chambers thereof.

4. The apparatus of claim 3, wherein first and second welds extend over opposing sides of the body portion of the balloon to form the first and second chambers thereof.

5. The apparatus of claim 1, wherein the balloon includes an elongated proximal neck and a distal neck, the body portion of the balloon extending between the elongated proximal neck and the distal neck, and the elongated proximal neck of the balloon is disposed proximal and distal to the side port of the outer shaft component.

6. The apparatus of claim 5, wherein a proximal cone extends between the elongated proximal neck and the body portion of the balloon and a distal cone extends between the distal neck and the body portion of the balloon, each of the proximal and distal cones extending between a 30 and 40 degree angle relative to the longitudinal axis of the apparatus.

7. The apparatus of claim 6, wherein the distal cone extends at a 30 degree angle relative to the longitudinal axis of the apparatus and the proximal cone extends at a 40 degree angle relative to the longitudinal axis of the apparatus.

8. The apparatus of claim 1, wherein the outer shaft component also includes a guidewire lumen that extends along at least a portion of the outer shaft component and terminates at a distal port at the distal end of the outer shaft component, the guidewire lumen of the outer shaft component being configured to slidingly receive a guidewire there-through.

9. The apparatus of claim 8, wherein a reinforced tubular component is disposed adjacent to the distal end of the outer shaft component and the reinforced tubular component defines a lumen in fluid communication with the guidewire lumen of the outer shaft component, the reinforced tubular component distally extending beyond the distal end of the outer shaft component through the balloon.

10. The apparatus of claim 9, wherein the reinforced tubular component includes a coiled element embedded within a polymer tube.

11. The apparatus of claim 1, wherein a proximal end of the needle housing is embedded into the outer shaft component.

12. The apparatus of claim 1, wherein the needle component has a curved distal end with the same curvature as the curved distal portion of the needle lumen of the outer shaft component and a distal tip of the needle component is configured to penetrate a wall of the vessel.

13. The apparatus of claim 12, wherein in a first configuration of the apparatus the curved distal end of the needle component is held in a straightened form within the needle housing and wherein in a second configuration of the apparatus the curved distal end of the needle component extends from the side port of the outer shaft component and bends from the longitudinal axis of the apparatus.

14. The apparatus of claim 12, wherein the needle component includes a straight segment disposed between the curved distal end and the distal tip.

15. The apparatus of claim 1, wherein a distal tip of the needle housing includes a skive cut forming an opening configured to embed into the outer shaft component.

16. An apparatus for bypassing an occlusion in a blood vessel comprising:
   an outer shaft component having a distal port at a distal end thereof and a side port proximal to the distal end thereof, the outer shaft component including a needle lumen there-through that includes a curved distal portion that bends from a longitudinal axis of the apparatus and terminates at the side port of the outer shaft component, an inflation lumen there-through configured to receive inflation fluid, and a guidewire lumen that extends along at least a portion of the outer shaft component and terminates at the distal port of the outer shaft component, the guidewire lumen of the outer shaft component being configured to slidingly receive a guidewire there-through;
   a needle housing disposed within the needle lumen of the outer shaft component, the needle housing including a curved distal portion that defines the curved distal portion of the needle lumen and a transition proximal portion that has a variable flexibility along its length that decreases in a distal direction;
   a needle component configured to be slidably disposed within the needle lumen of the outer shaft component and removable therefrom;
   an inflatable balloon disposed at the distal end of the outer shaft component and in fluid communication with the inflation lumen of the outer shaft component, the balloon including a body portion that is disposed distal to the distal end of the outer shaft component, the body portion of the balloon having a flattened profile in an inflated state with first and second chambers that laterally extend from opposing sides of the outer shaft component for stabilizing the apparatus within a subintimal space; and
   a reinforced tubular component disposed adjacent to the distal end of the outer shaft component, the reinforced tubular component distally extending beyond the distal end of the outer shaft component through the balloon, wherein the reinforced tubular component defines a lumen in fluid communication with the guidewire lumen of the outer shaft component.

17. The apparatus of claim 16, wherein the needle component has a curved distal end with the same curvature as the curved distal portion of the needle lumen of the outer shaft component and a distal tip of the needle component is configured to penetrate a wall of the vessel, and wherein in a first configuration of the apparatus the curved distal end of the needle component is held in a straightened form within the needle housing and wherein in a second configuration of the apparatus the curved distal end of the needle component extends from the side port of the outer shaft component and bends from the longitudinal axis of the apparatus.

18. The apparatus of claim 17, wherein the needle component includes a straight segment disposed between the curved distal end and the distal tip.

* * * * *